(12) United States Patent
Abeyratne et al.

(10) Patent No.: US 11,783,947 B2
(45) Date of Patent: Oct. 10, 2023

(54) METHOD AND APPARATUS FOR AUTOMATIC DISEASE STATE DIAGNOSIS

(71) Applicant: THE UNIVERSITY OF QUEENSLAND, St. Lucia (AU)

(72) Inventors: Udantha Abeyratne, St. Lucia (AU); Keegan Kosasih, St. Lucia (AU)

(73) Assignee: UNIVERSITY OF QUEENSLAND, St. Lucia (AU)

( * ) Notice: Subject to any disclaimer, the term of this patent is extended or adjusted under 35 U.S.C. 154(b) by 375 days.

(21) Appl. No.: 16/336,269

(22) PCT Filed: Sep. 26, 2017

(86) PCT No.: PCT/AU2017/051048
§ 371 (c)(1),
(2) Date: Mar. 25, 2019

(87) PCT Pub. No.: WO2018/053604
PCT Pub. Date: Mar. 29, 2018

(65) Prior Publication Data
US 2020/0027558 A1    Jan. 23, 2020

(30) Foreign Application Priority Data

Sep. 26, 2016  (AU) ................. 2016903894
Sep. 26, 2016  (AU) ................. 2016903896

(51) Int. Cl.
*G16H 50/20* (2018.01)
*A61B 5/08* (2006.01)
(Continued)

(52) U.S. Cl.
CPC .......... *G16H 50/20* (2018.01); *A61B 5/0823* (2013.01); *G06F 3/16* (2013.01); *G06F 9/542* (2013.01)

(58) Field of Classification Search
None
See application file for complete search history.

(56) References Cited

U.S. PATENT DOCUMENTS

2005/0065813 A1* 3/2005 Mishelevich .......... G16H 50/30
                                                                            705/2
2009/0094053 A1* 4/2009 Jung ...................... G06Q 10/00
                                                                            705/2
(Continued)

FOREIGN PATENT DOCUMENTS

CN      104321015      1/2015
CN      109788907      5/2019
(Continued)

OTHER PUBLICATIONS

International Search Report of PCT/AU2017/051048 dated Feb. 5, 2018, 3 pages.
(Continued)

*Primary Examiner* — Charles E Anya
(74) *Attorney, Agent, or Firm* — Nixon & Vanderhye PC

(57) ABSTRACT

A method of automatically diagnosing pneumonia in a patient includes using an input/output interface device to obtain values of two or more diagnostic parameters of the patient from a caregiver for the patient. The method includes using a processor coupled to the input/output interface to apply the two or more diagnostic parameters to an electronic memory storing precompiled pneumonia diagnostic models to identify an optimal diagnostic model for making a diagnosis. The values of the two or more diagnostic signs are applied to the identified optimal diagnostic model to generate a diagnosis output. The input/output interface device is operated in accordance with the diagnosis output to indicate the presence or absence of pneumonia in the patient to the caregiver. The caregiver may use the diagnosis to provide appropriate care to the patient. The pneumonia diagnostic
(Continued)

models are derived from investigation of a population of pneumonia positive and non-pneumonia subjects.

21 Claims, 18 Drawing Sheets

(51) Int. Cl.
*G06F 3/16* (2006.01)
*G06F 9/54* (2006.01)

(56) References Cited

U.S. PATENT DOCUMENTS

| | | |
|---|---|---|
| 2011/0270050 A1 | 11/2011 | Morteza et al. |
| 2012/0215076 A1 | 8/2012 | Yang et al. |
| 2014/0101080 A1 | 4/2014 | Lee et al. |
| 2014/0257058 A1 | 9/2014 | Clarysse et al. |
| 2015/0073306 A1* | 3/2015 | Abeyratne ............ A61B 5/742 600/586 |
| 2015/0204869 A1* | 7/2015 | Casals-Pascual ...... A61K 45/06 424/613 |
| 2015/0205916 A1* | 7/2015 | Yamamoto ............ G16H 80/00 702/19 |
| 2015/0245788 A1 | 9/2015 | Schmidt |
| 2017/0014079 A1* | 1/2017 | Lee ......................... A61B 8/54 |
| 2020/0027558 A1 | 1/2020 | Abeyratne et al. |

FOREIGN PATENT DOCUMENTS

| | | |
|---|---|---|
| JP | 2007-018460 | 1/2007 |
| JP | 2009-110282 | 5/2009 |
| WO | 2013/142908 | 10/2013 |
| WO | 2016/142360 | 9/2016 |

OTHER PUBLICATIONS

Extended European Search Report dated Apr. 1, 2020 in corresponding European Application No. 17852006, 11 pages.

Examination Report dated Jun. 15, 2022 in corresponding Australian Application No. 2017331813, 10 pages.

Examination Report dated Jan. 5, 2022 in corresponding Chinese Application No. 201780059397.3, 10 pages.

* cited by examiner

METHOD AND APPARATUS FOR AUTOMATIC DISEASE STATE DIAGNOSIS

This application is the U.S. national phase of International Application No. PCT/AU2017/051048 filed Sep. 26, 2017 which designated the U.S. and claims priority to AU Patent Application No. 2016903894 filed Sep. 26, 2016 and AU Patent Application No. 2016903896 filed Sep. 26, 2016, the entire contents of each of which are hereby incorporated by reference.

TECHNICAL FIELD

The present invention concerns methods and apparatus for assisting medical staff to diagnose and manage patients suffering from respiratory dysfunctions such as pneumonia.

RELATED APPLICATIONS

This application claims priority from Australian provisional patent applications Nos. 2016903894 and 2016903896, both filed 26 Sep. 2016, the disclosures of which are hereby incorporated herein in their entireties.

BACKGROUND ART

Any references to methods, apparatus or documents of the prior art are not to be taken as constituting any evidence or admission that they formed, or form part of the common general knowledge.

Pneumonia is one of the leading causes of mortality in children under five worldwide. It is estimated that 905,059 children below the age of five died from pneumonia globally in 2013 [ref 1]. It accounted for 14% of a total of 6.3 million child deaths around the world that year [1, 2]. The United Nations (UN) is aware of the issue and, through the Millenium Development Goal (MDG) 4 program, worked with countries globally to reduce the under-five mortality rate by two thirds in the period 1990 to 2015 [3-5].

Diagnostic tools used currently to diagnose pneumonia include stethoscopes and auscultation, chest X-ray, chest CT imaging, blood analysis, pulse oximetry, microbiology laboratory. There is no gold standard to diagnose pneumonia. The definitive diagnosis of childhood pneumonia, especially the early stage disease, is surprisingly difficult even in a hospital. Lung aspiration biopsy may be the most effective approach but it is clearly impractical for clinical use. The clinical examination and chest auscultation with a stethoscope are the first steps in diagnosing childhood pneumonia. Auscultation requires a skilled physician, and even then cannot provide a sensitive or specific enough diagnosis. Chest X-ray is often used as an important reference standard in confirming a clinical diagnosis. However, X-rays may not be sensitive to early stage pneumonia or when the diseased part of the lung is not clearly visible on the image. In addition, normal X-ray may lead to poor specificity of diagnosis in the presence of lung scarring or congestive heart disease. X-ray CT imaging (Computed Tomography) and other laboratory analyses such as sputum tests, blood culture and C-reactive protein (CRP) tests may be needed to differentially diagnose pneumonia in some cases. None of the tests mentioned above can be used as a gold standard. In hospitals in the developed world, the 'reference standard' used is the clinical diagnosis aided with auscultation, radiology, laboratory and microbiology as needed. Often, the suspicion of pneumonia is enough to prescribe antibiotics. Even in a hospital, it is difficult to separate viral wheeze from viral pneumonia, for instance (viral pneumonia is the most common form of pneumonia).

Throughout the world, the differential diagnosis of pneumonia and other respiratory disease is a complicated problem. Other illnesses that need to be resolved are: bronchiolitis, asthma, viral wheeze, pneumonia, tracheobroncomalacia (TBM) and croup—all in children. Malaria and congestive heart disease too can be symptomatically similar. In general diagnosing them is quite difficult even in a hospital setting. Long term monitoring at a home/community setting is next to impossible.

In resource-poor areas of the world where pneumonia is rampant, it is also difficult to find trained healthcare personnel with expert auscultation and clinical skills. The management of pneumonia in such regions is largely dependent on community workers who visit remote communities.

In order to address these problems, the World Health Organization (WHO) has developed a simple clinical procedure to classify pneumonia in resource-limited regions. These classifications directly lead to interventions such as antibiotic prescription and hospitalization. The WHO procedure uses the symptom of cough (and/or breathing difficulty) as the screening-in feature for pneumonia; breathing rate then determines if pneumonia exists. The disease will be further classified as severe pneumonia if symptoms such as chest recession are also present.

Even though the breathing rate based WHO procedures perform poorly, in remote areas where over 90% of childhood pneumonia occur, it is the main pneumonia classification methods used to determine treatment/referral decisions.

In the past, several studies have explored the performance of the WHO procedure and its variants in pneumonia diagnosis. They reported a reasonably high sensitivity (69-94%) but an unacceptably poor specificity (67-16%). Researchers have attempted to improve the specificity of the WHO criteria using different approaches. These include the augmentation of WHO procedure by considering fever and other symptoms of pneumonia (nasal flaring, poor sleep, chest in-drawing, cough lasting longer than two days etc.). These efforts resulted in a sensitivity and specificity within the range 20-90%, but higher specificities were achieved only at the cost of lower sensitivity and vice versa. They also suffer from the fact that the higher the complexity of measurements, the more difficult it is to train community workers to reliably implement the procedure in field visits.

The WHO procedure uses breathing rate as the key measurement. However, obtaining the breathing rate is notoriously difficult in children. A vast amount of resources have been committed by agencies such as the Bill & Melinda Gates Foundation, Unicef and WHO to develop breathing rate counters. See https://www.path.org/publications/files/TS_update_rr_counters.pdf for an example. In the manual diagnosis of pneumonia, different clinical signs and measurements are dichotomized for the ease of assessment by a clinician. For instance, breathing rates above age indexed thresholds are used to declare the existence of pneumonia. Clinicians may also note the existence/absence of cough, fever, chest-in-drawing etc.

An issue with using only cough sounds is the number of coughs required (5-10 cough events) for reliable analysis. It is known that infant patients may not readily cough when required in order to use it for analysis. Furthermore, as the patient's condition gets worse, it is also known that cough symptoms may vanish due to their having a weakened body.

It will therefore be realised that one of the key developments still missing in the global fight against pneumonia is the absence of a rapid, low cost diagnostic method/system[1, 8-14]. Diagnosing each case accurately and precisely is difficult even with state of the art equipment, and even more so in poor resource settings.

It is an object of the present invention to provide a method and apparatus for assisting in the diagnosis of a disease state such as pneumonia which is straightforward for a clinician to use and which addresses one or more of the above described problems of the prior art.

SUMMARY OF THE INVENTION

According to a first aspect of the present invention there is provided a method for automatically providing a carer of a patient with a disease state diagnosis of the patient including the steps of:
  providing a diagnostic application software product including a multiplicity of diagnostic models derived from investigation of a population containing disease state positive and non-disease state subjects;
  operating an input/output interface of an electronic device including a memory storing the software product to prompt the carer for identification of a number of disease diagnostic parameters and values therefor for the patient;
  operating a processor of the electronic device to select one of the diagnostic models from the memory based on the identified disease diagnostic parameters;
  operating the processor to apply the values of the disease diagnostic parameters to the selected diagnostic model; and
  presenting a diagnosis to the carer on the input/output interface based upon results of the application of the parameters to the selected diagnostic model for the carer to use in providing therapy to the patient.

Preferably said diagnostic parameters comprise: breathing rate, existence of fever, existence of runny nose, number of days with runny nose, number of days with cough, existence of chest indrawing, temperature, BMI (body mass index), and oxygen saturation level;

In an embodiment of the invention the method includes selecting one of the diagnostic models with reference to one or more look up tables correlating diagnostic performance of models against available diagnostic parameters.

The method may include prompting for user choice of a diagnostic model optimized for "sensitivity", "specificity" or "accuracy" wherein the method includes operating the electronic device to select one of the diagnostic models taking into account the optimization choice.

In an embodiment the method includes operating the device to determine if the values of diagnostic parameters indicate patient danger signs.

The method may include checking if the diagnostic values for the patient indicate that the patient is presenting general danger signs according to World Health Guidelines.

The method may include saving diagnostic results to a remote server whereby diagnostic results may be saved and compared from a plurality of diagnostic devices.

In some embodiments of the invention the method includes prompting for recording of at least one patient cough sound.

The method may include requiring the recording of no more than two patient cough sounds.

Preferably the method includes applying the at least one patient cough sound to a cough feature extraction engine of the diagnostic application to generate cough features.

The patient cough features may be applied to the diagnostic model to assist the diagnosis.

In a preferred embodiment of the invention the diagnostic parameters comprise breathing rate, temperature, heart rate and cough sound analysis.

According to another aspect of the present invention there is provided a diagnostic device arranged to prompt a clinician to input diagnostic information for a patient and further arranged to automatically present a diagnosis to the clinician, the diagnostic device including:
  an electronic memory storing instructions comprising a diagnostic application software product including a plurality of diagnostic models derived from investigation of pneumonia-positive and non-pneumonia subjects;
  an electronic processor in communication with the electronic memory for executing the instructions;
  a user interface responsive to the electronic processor for the processor to prompt for and receive the diagnostic information;
  wherein the processor is configured by the diagnostic application in use to present a diagnosis of the patient with the user interface by applying the diagnostic information to at least one of said diagnostic models.

Preferably the diagnostic device includes a microphone and audio interface coupling the microphone to the electronic processor.

The diagnostic application may include a cough feature extraction engine and whereby in use the processor applies the cough sound to the cough feature extraction engine to produce cough features thereof.

In an embodiment of the invention the diagnostic device is configured by the diagnostic application in use to apply the cough features to the at least one of said diagnostic models.

According to a further aspect of the present invention there is provided a method of automatically diagnosing pneumonia in a patient comprising:
  using an input/output interface device to obtain values of two or more diagnostic parameters of the patient from a carer for the patient;
  said diagnostic parameters comprising: breathing rate, existence of fever, existence of runny nose, number of days with runny nose, number of days with cough, existence of chest indrawing, temperature, BMI (body mass index), and oxygen saturation level;
  using a processor device operatively coupled to the input/output interface to apply the two or more diagnostic parameters to an electronic memory storing a plurality of precompiled pneumonia diagnostic models to thereby identify an optimal diagnostic model of said plurality;
  applying the values of the two or more diagnostic parameters to the identified optimal diagnostic model to generate a diagnosis output from the diagnostic model; and
  operating the input/output interface device in accordance with the diagnosis output to indicate presence or absence of pneumonia in the patient to the carer, for use by the carer in providing care to the patient;
  wherein the pneumonia diagnostic models are derived from investigation of a population of pneumonia positive patients and non-pneumonia positive subjects.

According to another aspect of the present invention there is provided a method for operating an electronic processor based electronic device to diagnose a disease state of a patient including the steps of:

installing a diagnostic application software product on the electronic device, the diagnostic application including a multiplicity of diagnostic models;

prompting for identification of a number of disease diagnostic parameters and values therefor for the patient;

operating the electronic device to select one of the diagnostic models based on the identified disease diagnostic parameters;

operating the electronic device to apply the values of the disease diagnostic parameters to the selected diagnostic model; and presenting a diagnosis to the clinician based upon results of the application of the parameters to the selected diagnostic model.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows:

FIGS. 11A to 11D are screens generated by the diagnostic device of FIG. 11A for prompting for cough sounds of the patient and for analyzing and presenting diagnostic results for the patient.

DETAILED DESCRIPTION OF PREFERRED EMBODIMENTS

Figure 1:
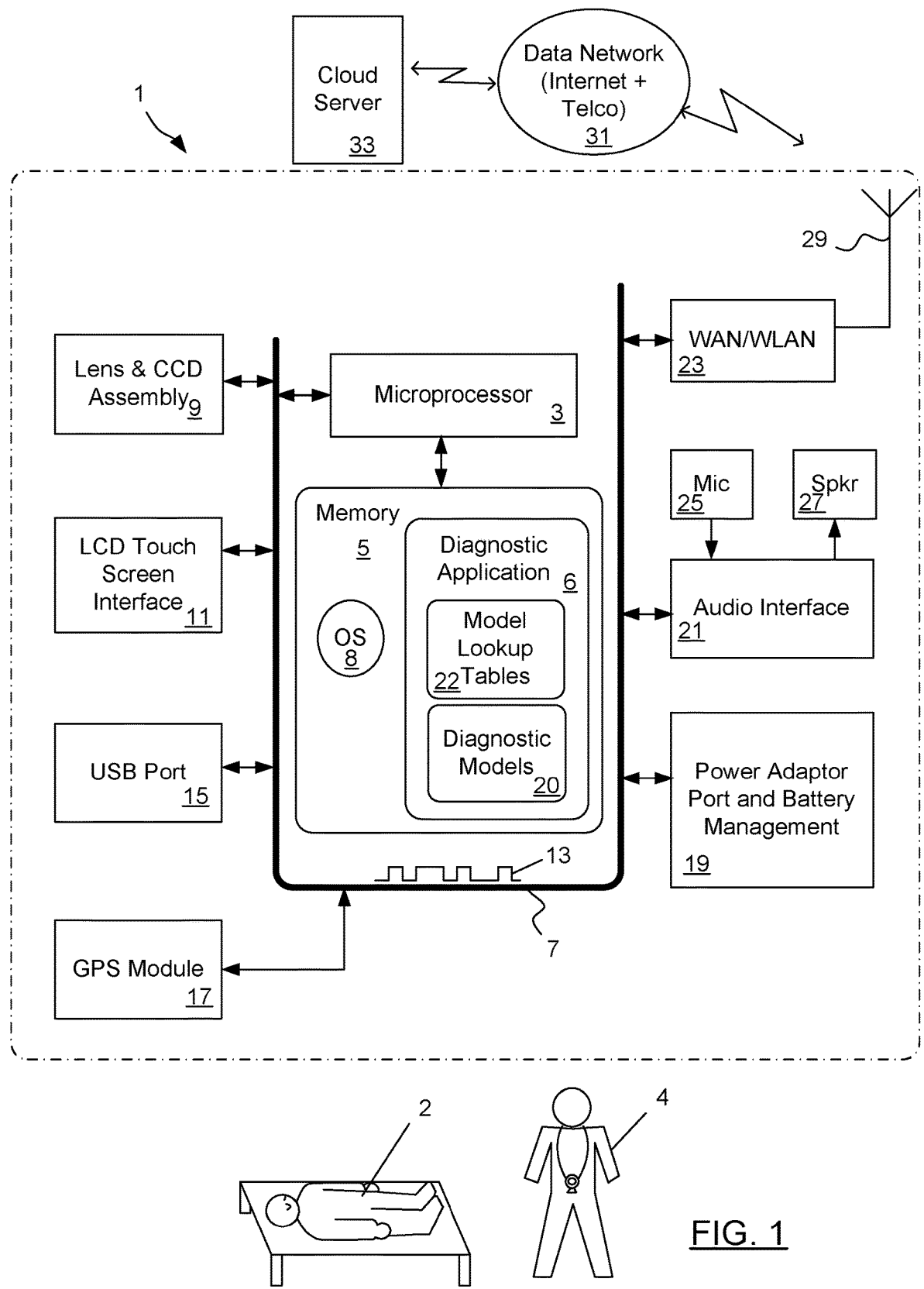
FIG. 1 is a block diagram of a diagnostic device according to an embodiment of the present invention shown in use.

Referring initially to FIG. 1 there is shown a diagnostic device 1 according to an embodiment of the present invention. The diagnostic device 1 comprises a unique combination of hardware and software specifically designed to assist a clinician to diagnose, and so be able to treat, a disease state such as pneumonia. In the embodiment of the invention that is illustrated in FIG. 1 the device 1 includes one or more processors in the form of microprocessor 3 and an electronic memory 5 that is accessible to the microprocessor 3 and which stores instructions that are executable by the microprocessor 3 in order for the diagnostic device 1 to process diagnostic signs of a patient 2 and present a diagnosis to carer in the form of clinician 4. The Diagnostic application 6 includes a plurality of diagnostic models 20 which are stored in memory 5 and a model lookup table 22 which the microprocessor 3 uses to determine the most appropriate diagnostic model based on available diagnostic parameters for a patient 2. As is explained in Appendix B of this specification, with reference to Table 9, the Inventors drew on their quantitative research of over 131,000 combinations of features associated with pneumonia to arrive at the diagnostic models that are used.

The electronic memory 5 includes an operating system 8 such as the Android operating system or the Apple iOS operating system, for example, for execution by the microprocessor 3. The electronic memory 5 also includes a diagnostic application software product 6 according to a preferred embodiment of the present invention.

The microprocessor 3 is in data communication with a plurality of peripheral assemblies 9 to 23, as indicated in FIG. 1, via a data bus 7. The data bus consists of metal tracks which convey electrical data signals 13 between the various assemblies of the device 1. The diagnostic device 1 is able to establish voice and data communication with a voice and/or data communications network 31 via WAN/WLAN assembly 23 and radio frequency antenna 29.

Although the diagnostic device 1 that is illustrated in FIG. 1 is microprocessor based it will be realised that it could also be implemented using other types of technology. For example it could be implemented using a Field Programmable Gate Array (FPGA) or discrete logic circuits.

The diagnostic device 1 requires no external physiological sensors, physical contact with patient 2 or access to communication network 31 to operate. As will be explained the method is automated and straightforward to use. In some embodiments the device 1 collects patient metadata, diagnosis and treatment/referral information (e.g. whether or not an antibiotic was dispensed) along with GPS coordinates at the site of the diagnosis. The device logs the information or will transfer it over a WAN data network, 31, e.g. the Internet, to a cloud server 33 when/if network 31 is available. In one embodiment the device makes it possible to track pandemics. It can also take into account developing epidemics in diagnosing patients by accessing geographical information stored in the cloud server 33 of the diagnosis of disease in other locations using similar devices.

Figure 2:
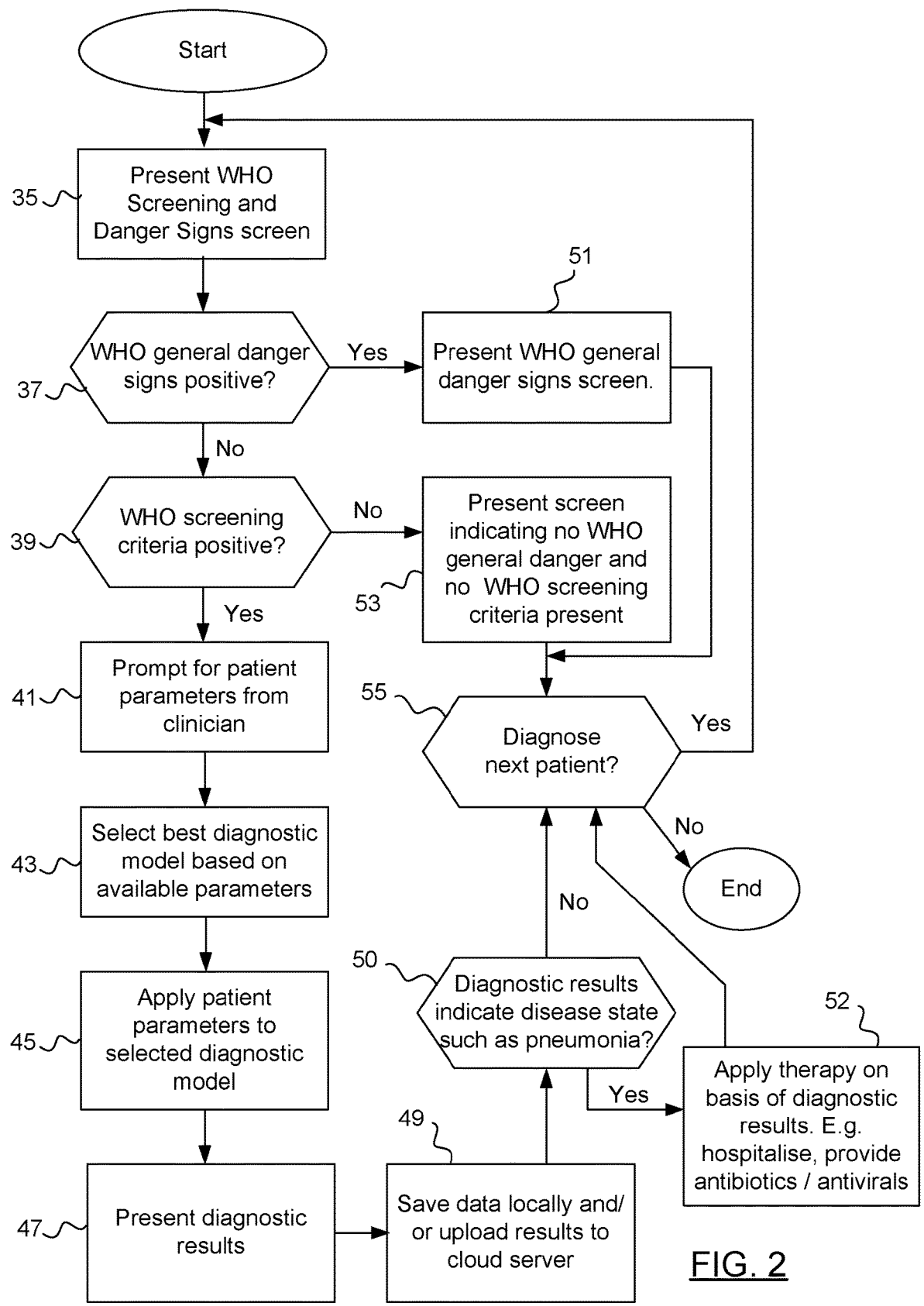
FIG. 2 is a flowchart of a method performed by the diagnostic device of FIG. 1 in accordance an embodiment of the invention.

Referring now to FIG. 2, there is shown a flowchart of a method according to a preferred embodiment of the present invention, which the diagnostic device implements under the control of the instructions that are coded into the diagnostic application 6.

Figure 3:
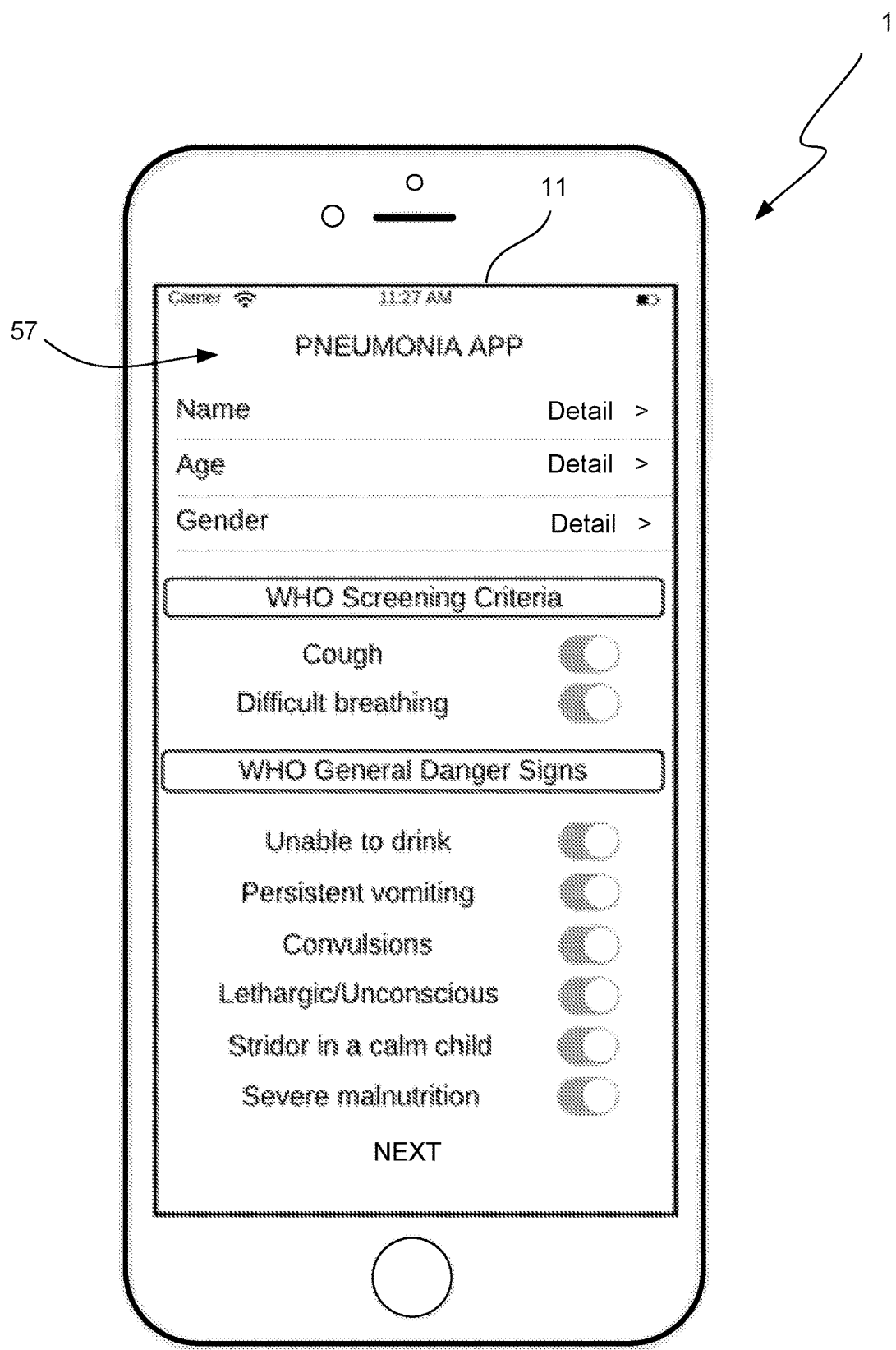
FIGS. 3 to 5 depict screens generated by the diagnostic device for detecting WHO general danger signs of a patient.

At box 35 of FIG. 2, the microprocessor 3 operates an input/output interface in the form of LCD touch screen interface 11 to display a prompt for a user, e.g. clinician 4, to enter diagnostic parameters of patient 2. FIG. 3 shows the diagnostic device 1 displaying a data entry screen 57 on LCD touch screen interface 11 for the clinician 4 to enter the patient parameters.

The diagnostic program 6 includes instructions based on the Inventors' finding that there are at least 17 patient parameters that may be of use in diagnosing a disease state, such as pneumonia as shown in Table 1A below:

TABLE 1A

Seventeen Diagnostic Parameters for Pneumonia

| | |
|---|---|
| Age | Months |
| Weight | Kg |
| Height | m |
| Breathing rate | Breaths/min |
| Heart rate | Beats/min |
| Temperature | ° C. |
| BMI | Number |
| Oxygen saturation | Percentage |
| Chest indrawing | Yes/No |
| Fever | Yes/No |
| Days with fever | Days |
| Cough | Yes/No |
| Days with cough | Days |
| Runny nose | Yes/No |
| Days with runny nose | Days |
| Breathing difficulty | Yes/No |
| Days with breathing difficulty | Days |

The Inventors have discovered that the most straightforward patient parameters to obtain and which are effective in determining the presence of a respiratory disease state such as pneumonia are the nine diagnostic parameters that are set out in table 1B below.

TABLE 1B

Subset of Nine Important Patient Diagnostic Sign Parameters

| Code | Diagnostic Sign |
|---|---|
| A | Breathing rate |
| B | Fever |
| C | Existence of runny nose |
| D | Days with runny nose |
| E | Days with cough |
| F | Chest indrawing |
| G | Temperature |
| H | BMI |
| I | Oxygen saturation |
| — | Not used |

Figure 4:
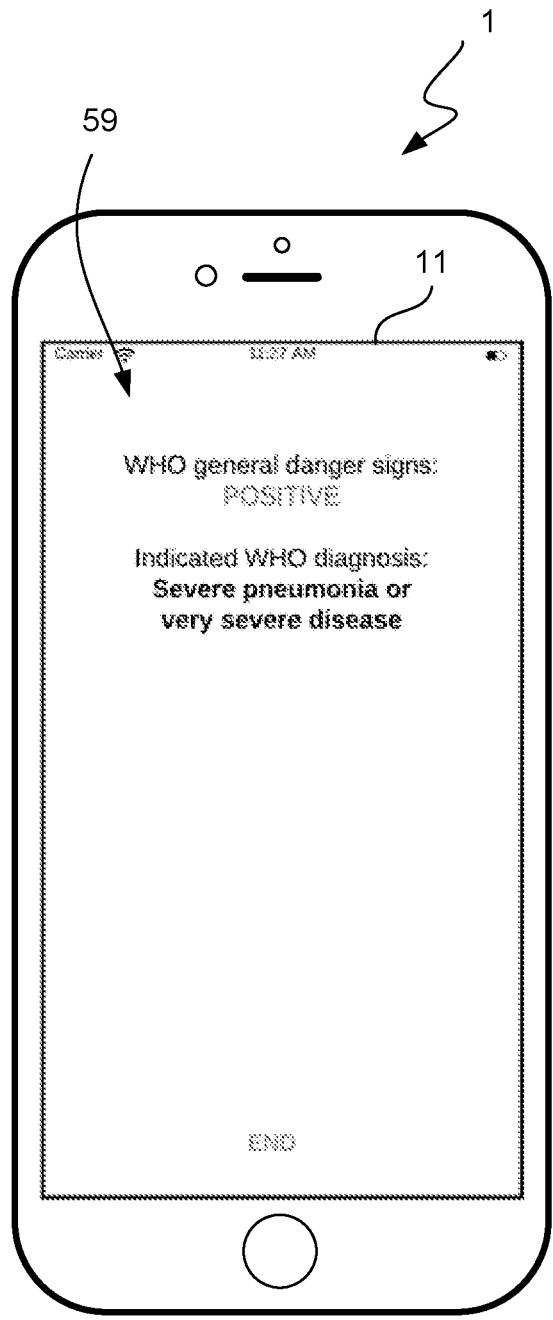
Figure 5:
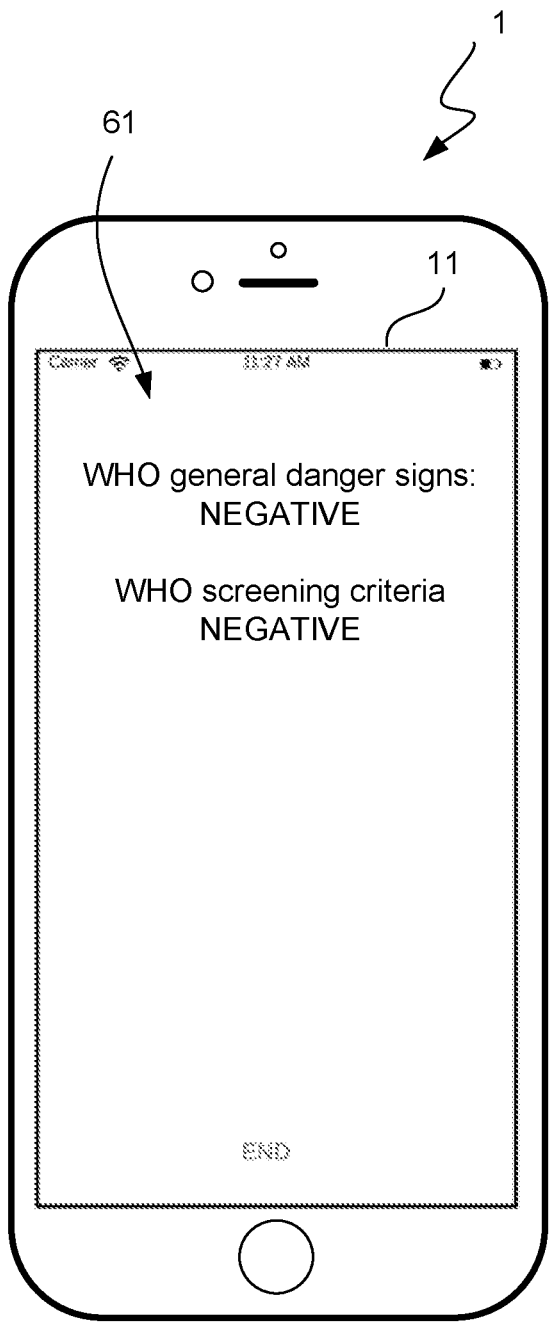

A preferred embodiment of diagnostic device 1 is configured to operate in the World Health Organization (WHO) framework and this can be seen in the way that the screen 57 provides for the clinician 4 to select WHO Screening Criteria, namely "Cough" and "Difficulty Breathing" and also to enter WHO General Danger Signs as listed in screen 57. At box 37 of the flowchart of FIG. 2, if the clinician 4 has indicated on screen 57 that the patient 2 is displaying WHO general danger signs then microprocessor control diverts to box 51 at which point the microprocessor 3 operates screen 59 (FIG. 4) to alert the clinician 4 that the patient 2 is indicating severe pneumonia or disease according to the WHO general danger signs criteria. Alternatively, if at box 37 the patients' parameters do not indicate the WHO general danger signs then control diverts to box 39. At box 39 the microprocessor checks whether the patient parameters indicate that the WHO criteria for further screening have been met. If they have not been met then control diverts to box 53 at which point the microprocessor 5 causes the screen 61 that is shown in FIG. 5 to display thereby indicating to the clinician 4 that the patient 2 exhibits neither the WHO general danger signs nor the WHO screening criteria.

Alternatively, if at box 39 the microprocessor 5, executing a further instruction of diagnostic application 6, determines that the patient's parameters indicate that the WHO screening criteria parameters are met then control diverts to box 41.

Figure 6:
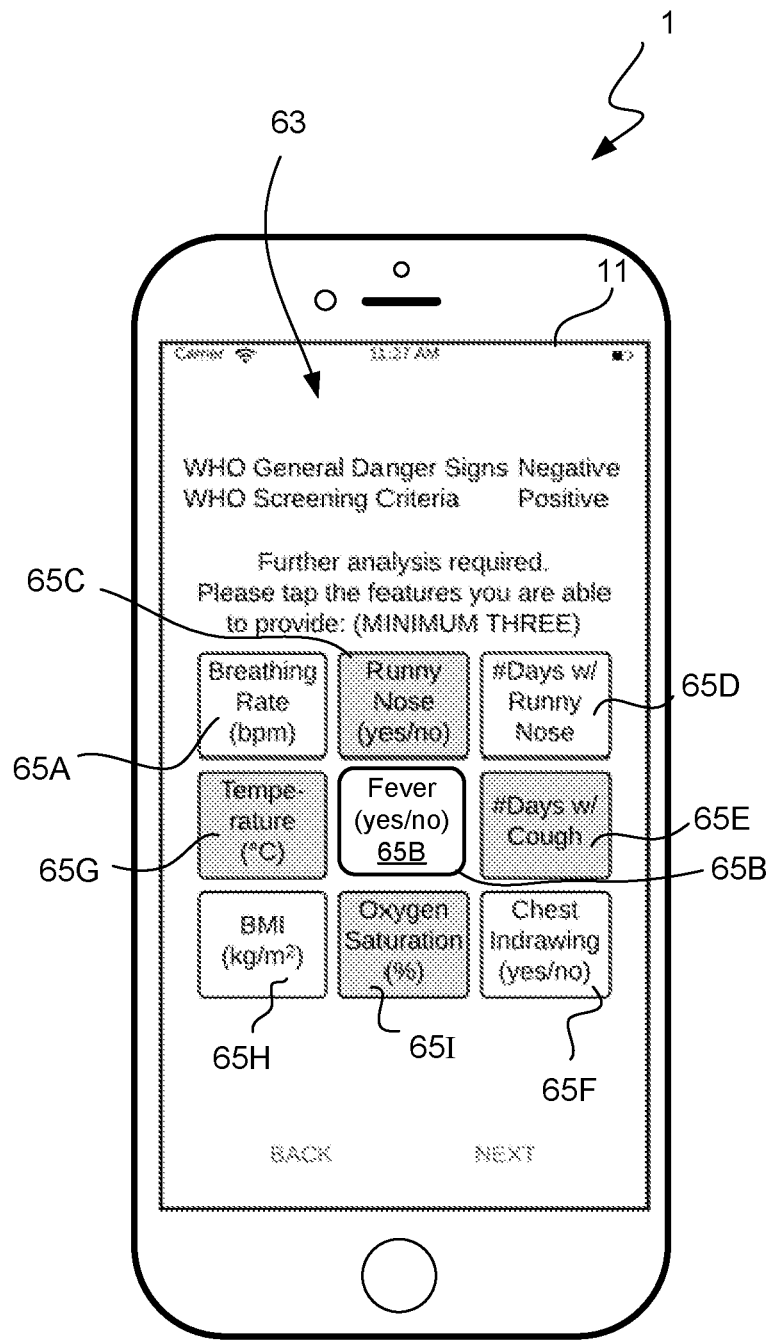
FIG. 6 depicts a screen generated by the diagnostic device for a clinician to enter diagnostic information for a patient.

At box 41 the microprocessor 5 causes screen 63 (FIG. 6) to display on LCD touchscreen 11 to prompt for patient diagnostic parameters from the clinician 4.

Screen 63 presents selection buttons 65A, . . . ,65I for the nine patient parameters that have previously been referred to in Table 1 B.

Figure 7:
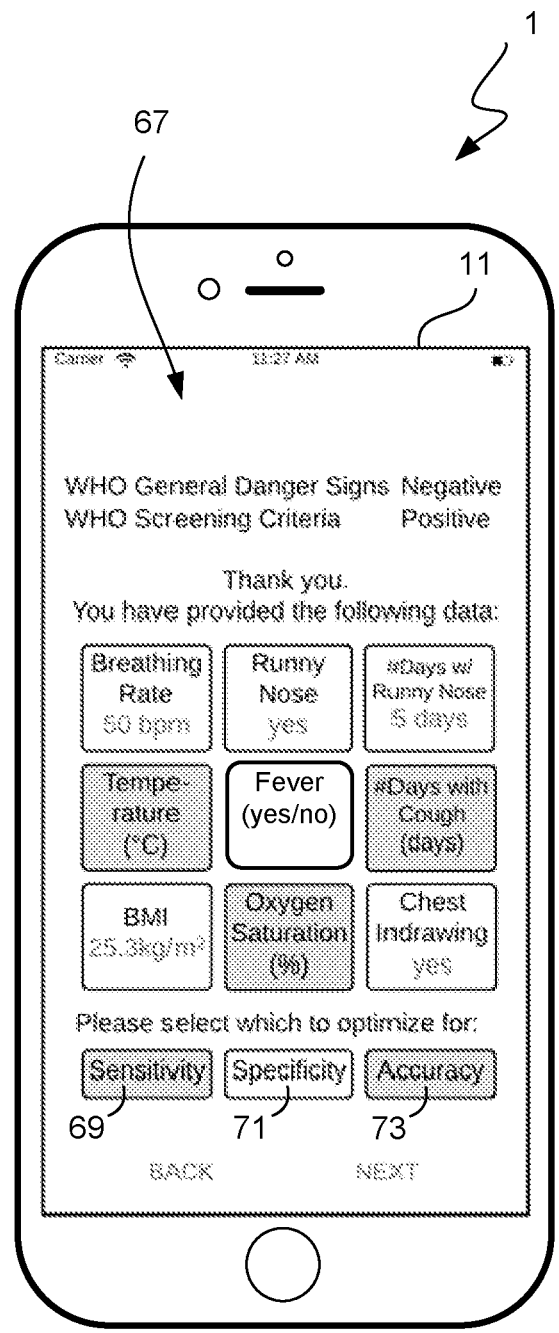
FIG. 7 depicts a screen generated by the diagnostic device to confirm the entered diagnostic information to the clinician.

In the presently described embodiment the clinician 4 is required to select at least three of the diagnostic parameters of Table 1B by means of the selection buttons 65A . . . ,65I. Control then diverts to box 43 (FIG. 2) wherein microprocessor 3 displays screen 67 (FIG. 7) on interface 11. In the presently described preferred embodiment of the invention screen 67 includes selection buttons 69, 71 and 73 for clinician 4 to indicate a preference for the diagnostic model that will be used to optimize for any one of diagnostic "sensitivity", "specificity" or "accuracy". These terms have the following meanings:

Sensitivity: (also called the true positive rate, the recall, or probability of detection in some fields) measures the proportion of positives that are correctly identified as such (e.g., the percentage of sick people who are correctly identified as having the condition).

Specificity: (also called the true negative rate) measures the proportion of negatives that are correctly identified as such (e.g., the percentage of healthy people who are correctly identified as not having the condition).

Accuracy: (ACC)=(ΣTrue positive+ΣTrue negative)/ΣTotal population

At box 43, the microprocessor 3 selects the optimal diagnostic model, amongst models 20 which are stored in memory 5, based on the patient parameters that have been submitted. To select the best of models 20 for the information that the clinician has entered, the microprocessor 3, as configured by diagnostic program 6, queries diagnostic model lookup tables 22 which are stored in memory 5 and which the Inventors have produced. (It will be realised that in other embodiments of the invention, wherein a high power processor is used, it may be possible to generate the required information as required without resort to look up tables.)

The content of the diagnostic lookup tables 22 is set out as follows:

Table 2A—Patient 2 to 11 Months of Age—Diagnostic Model Ordered According to Descending Sensitivity.
Table 2B—Patient 2 to 11 Months of Age—Diagnostic Model Ordered According to Descending Specificity
Table 2C—Patient 2 to 11 Months of Age—Diagnostic Model Ordered According to Descending Specificity.
Table 3A—Patient 12 to 60 Months of Age—Diagnostic Model Ordered According to Descending Sensitivity
Table 3B—Patient 12 to 60 Months of Age—Diagnostic Model Ordered According to Descending Specificity.
Table 3C—Patient 12 to 60 Months of Age—Diagnostic Model Ordered According to Descending Accuracy.

The patient diagnostic sign parameters that make up each combination in the combination columns of the following Tables 2A to C have previously been defined in Table 1B.

TABLE 2A

Patient 2 to 11 Months of Age - Diagnostic Model Ordered According to Descending Sensitivity.

Ordered according to descending sensitivity

| No | Combination | SEN (%) | SPE (%) | ACC (%) | PPV (%) | NPV (%) |
|---|---|---|---|---|---|---|
| 1 | CEF- | 96 | 50 | 77 | 74 | 81 |
| 2 | EFI- | 94 | 54 | 77 | 76 | 85 |
| 3 | CDF- | 92 | 52 | 74 | 74 | 73 |
| 4 | CDEF | 92 | 56 | 76 | 74 | 86 |
| 5 | ACDI | 91 | 70 | 82 | 82 | 89 |
| 6 | ACFG | 91 | 50 | 73 | 73 | 77 |
| 7 | ABCD | 91 | 61 | 77 | 76 | 88 |
| 8 | ABI- | 91 | 51 | 73 | 72 | 85 |
| 9 | ABCI | 91 | 51 | 73 | 72 | 85 |
| 10 | BFI- | 91 | 58 | 78 | 75 | 86 |
| 11 | BCFI | 91 | 58 | 78 | 75 | 86 |
| 12 | BFGI | 91 | 58 | 78 | 75 | 86 |
| 13 | ACDH | 89 | 64 | 77 | 78 | 74 |
| 14 | CEFI | 89 | 57 | 77 | 76 | 81 |
| 15 | DEFI | 89 | 55 | 76 | 74 | 81 |
| 16 | ACDG | 89 | 53 | 73 | 73 | 72 |
| 17 | AFH- | 89 | 50 | 72 | 72 | 71 |
| 18 | ADI- | 89 | 54 | 75 | 74 | 83 |
| 19 | ADEI | 89 | 55 | 75 | 73 | 83 |
| 20 | AEF- | 89 | 54 | 73 | 72 | 77 |
| 21 | AEFH | 89 | 54 | 73 | 73 | 73 |
| 22 | BEFI | 88 | 64 | 79 | 80 | 79 |
| 23 | BEF- | 88 | 66 | 79 | 79 | 84 |
| 24 | BCEF | 88 | 66 | 79 | 79 | 84 |
| 25 | BFHI | 88 | 62 | 78 | 77 | 83 |
| 26 | BFH- | 88 | 62 | 78 | 76 | 82 |
| 27 | BFGH | 88 | 62 | 78 | 76 | 82 |
| 28 | BEFG | 88 | 59 | 76 | 75 | 82 |
| 29 | ABFI | 88 | 56 | 75 | 73 | 81 |

TABLE 2A-continued

Patient 2 to 11 Months of Age - Diagnostic Model Ordered According to Descending Sensitivity.

Ordered according to descending sensitivity

| No | Combination | SEN (%) | SPE (%) | ACC (%) | PPV (%) | NPV (%) |
|---|---|---|---|---|---|---|
| 30 | BCFH | 88 | 54 | 75 | 73 | 80 |
| 31 | ABEI | 88 | 51 | 72 | 71 | 81 |
| 32 | ACD- | 88 | 66 | 76 | 77 | 78 |
| 33 | EFGI | 88 | 53 | 74 | 74 | 77 |
| 34 | ACDE | 88 | 60 | 73 | 75 | 78 |
| 35 | ACDF | 87 | 53 | 71 | 73 | 71 |
| 36 | EFHI | 87 | 64 | 79 | 79 | 82 |
| 37 | BCDF | 87 | 51 | 72 | 72 | 77 |
| 38 | AFHI | 87 | 50 | 72 | 72 | 77 |
| 39 | CDHI | 86 | 54 | 76 | 74 | 75 |
| 40 | BDEF | 86 | 66 | 78 | 79 | 82 |
| 41 | BEFH | 86 | 64 | 76 | 77 | 81 |
| 42 | ABF- | 86 | 56 | 74 | 72 | 80 |
| 43 | ABCF | 86 | 56 | 74 | 72 | 80 |
| 44 | ADHI | 86 | 51 | 72 | 72 | 79 |
| 45 | ABC- | 86 | 53 | 70 | 70 | 78 |
| 46 | AB-- | 86 | 50 | 69 | 69 | 78 |
| 47 | FGHI | 86 | 54 | 74 | 73 | 80 |
| 48 | ADFI | 85 | 58 | 75 | 74 | 82 |
| 49 | DFHI | 85 | 53 | 74 | 73 | 0 |
| 50 | ABFH | 84 | 59 | 74 | 73 | 78 |
| 51 | ABEF | 84 | 59 | 73 | 73 | 79 |
| 52 | ABE- | 84 | 57 | 71 | 71 | 78 |
| 53 | ABCE | 84 | 57 | 71 | 71 | 78 |
| 54 | ABH- | 84 | 53 | 69 | 69 | 76 |
| 55 | ABCH | 84 | 53 | 69 | 69 | 76 |
| 56 | ABFG | 84 | 52 | 70 | 70 | 76 |
| 57 | ABG- | 84 | 54 | 69 | 70 | 77 |
| 58 | ABEG | 81 | 57 | 69 | 70 | 76 |
| 59 | ABEH | 81 | 57 | 69 | 70 | 76 |
| 60 | ABCG | 81 | 52 | 66 | 69 | 74 |
| 61 | DEHI | 77 | 57 | 73 | 73 | 67 |

TABLE 2B

Patient 2 to 11 Months of Age - Diagnostic Mode Ordered According to Descending Specificity Ordered according to descending specificity

| No | Combination | SEN (%) | SPE (%) | ACC (%) | PPV (%) | NPV (%) |
|---|---|---|---|---|---|---|
| 1 | ACDI | 91 | 70 | 82 | 82 | 89 |
| 2 | BEF- | 88 | 66 | 79 | 79 | 84 |
| 3 | BCEF | 88 | 66 | 79 | 79 | 84 |
| 4 | BDEF | 86 | 66 | 78 | 79 | 82 |
| 5 | ACD- | 88 | 66 | 76 | 77 | 78 |
| 6 | BEFI | 88 | 64 | 79 | 80 | 79 |
| 7 | EFHI | 87 | 64 | 79 | 79 | 82 |
| 8 | ACDH | 89 | 64 | 77 | 78 | 74 |
| 9 | BEFH | 86 | 64 | 76 | 77 | 81 |
| 10 | BFHI | 88 | 62 | 78 | 77 | 83 |
| 11 | BFH- | 88 | 62 | 78 | 76 | 82 |
| 12 | BFGH | 88 | 62 | 78 | 76 | 82 |
| 13 | ABCD | 91 | 61 | 77 | 76 | 88 |
| 14 | ACDE | 88 | 60 | 73 | 75 | 78 |
| 15 | BEFG | 88 | 59 | 76 | 75 | 82 |
| 16 | ABFH | 84 | 59 | 74 | 73 | 78 |
| 17 | ABEF | 84 | 59 | 73 | 73 | 79 |
| 18 | BFI- | 91 | 58 | 78 | 75 | 86 |
| 19 | BCFI | 91 | 58 | 78 | 75 | 86 |
| 20 | BFGI | 91 | 58 | 78 | 75 | 86 |
| 21 | ADFI | 85 | 58 | 75 | 74 | 82 |
| 22 | CEFI | 89 | 57 | 77 | 76 | 81 |
| 23 | DEHI | 77 | 57 | 73 | 73 | 67 |
| 24 | ABE- | 84 | 57 | 71 | 71 | 78 |
| 25 | ABCE | 84 | 57 | 71 | 71 | 78 |
| 26 | ABEG | 81 | 57 | 69 | 70 | 76 |

TABLE 2B-continued

Patient 2 to 11 Months of Age - Diagnostic Mode
Ordered According to Descending Specificity Ordered according to descending specificity

| No | Combination | SEN (%) | SPE (%) | ACC (%) | PPV (%) | NPV (%) |
|---|---|---|---|---|---|---|
| 27 | ABEH | 81 | 57 | 69 | 70 | 76 |
| 28 | ABFI | 88 | 56 | 75 | 73 | 81 |
| 29 | ABF- | 86 | 56 | 74 | 72 | 80 |
| 30 | ABCF | 86 | 56 | 74 | 72 | 80 |
| 31 | CDEF | 92 | 56 | 76 | 74 | 86 |
| 32 | DEFI | 89 | 55 | 76 | 74 | 81 |
| 33 | ADEI | 89 | 55 | 75 | 73 | 83 |
| 34 | ABG- | 84 | 54 | 69 | 70 | 77 |
| 35 | AEF- | 89 | 54 | 73 | 72 | 77 |
| 36 | AEFH | 89 | 54 | 73 | 73 | 73 |
| 37 | EFI- | 94 | 54 | 77 | 76 | 85 |
| 38 | ADI- | 89 | 54 | 75 | 74 | 83 |
| 39 | CDHI | 86 | 54 | 76 | 74 | 75 |
| 40 | BCFH | 88 | 54 | 75 | 73 | 80 |
| 41 | FGHI | 86 | 54 | 74 | 73 | 80 |
| 42 | EFGI | 88 | 53 | 74 | 74 | 77 |
| 43 | DFHI | 85 | 53 | 74 | 73 | 0 |
| 44 | ACDG | 89 | 53 | 73 | 73 | 72 |
| 45 | ACDF | 87 | 53 | 71 | 73 | 71 |
| 46 | ABC- | 86 | 53 | 70 | 70 | 78 |
| 47 | ABH- | 84 | 53 | 69 | 69 | 76 |
| 48 | ABCH | 84 | 53 | 69 | 69 | 76 |
| 49 | ABFG | 84 | 52 | 70 | 70 | 76 |
| 50 | ABCG | 81 | 52 | 66 | 69 | 74 |
| 51 | CDF- | 92 | 52 | 74 | 74 | 73 |
| 52 | ADHI | 86 | 51 | 72 | 72 | 79 |
| 53 | BCDF | 87 | 51 | 72 | 72 | 77 |
| 54 | ABI- | 91 | 51 | 73 | 72 | 85 |
| 55 | ABCI | 91 | 51 | 73 | 72 | 85 |
| 56 | ABEI | 88 | 51 | 72 | 71 | 81 |
| 57 | CEF- | 96 | 50 | 77 | 74 | 81 |
| 58 | AFHI | 87 | 50 | 72 | 72 | 77 |
| 59 | AB-- | 86 | 50 | 69 | 69 | 78 |
| 60 | ACFG | 91 | 50 | 73 | 73 | 77 |
| 61 | AFH- | 89 | 50 | 72 | 72 | 71 |

TABLE 2C

Patient 2 to 11 Months of Age - Diagnostic Model
Ordered According to Descending Specificity.

Ordered according to descending accuracy

| No | Combination | SEN (%) | SPE (%) | ACC (%) | PPV (%) | NPV (%) |
|---|---|---|---|---|---|---|
| 1 | ACDI | 91 | 70 | 82 | 82 | 89 |
| 2 | BEF- | 88 | 66 | 79 | 79 | 84 |
| 3 | BCEF | 88 | 66 | 79 | 79 | 84 |
| 4 | EFHI | 87 | 64 | 79 | 79 | 82 |
| 5 | BEFI | 88 | 64 | 79 | 80 | 79 |
| 6 | BFHI | 88 | 62 | 78 | 77 | 83 |
| 7 | BFI- | 91 | 58 | 78 | 75 | 86 |
| 8 | BCFI | 91 | 58 | 78 | 75 | 86 |
| 9 | BFGI | 91 | 58 | 78 | 75 | 86 |
| 10 | BDEF | 86 | 66 | 78 | 79 | 82 |
| 11 | BFH- | 88 | 62 | 78 | 76 | 82 |
| 12 | BFGH | 88 | 62 | 78 | 76 | 82 |
| 13 | CEF- | 96 | 50 | 77 | 74 | 81 |
| 14 | ABCD | 91 | 61 | 77 | 76 | 88 |
| 15 | ACDH | 89 | 64 | 77 | 78 | 74 |
| 16 | EFI- | 94 | 54 | 77 | 76 | 85 |
| 17 | CEFI | 89 | 57 | 77 | 76 | 81 |
| 18 | BEFH | 86 | 64 | 76 | 77 | 81 |
| 19 | BEFG | 88 | 59 | 76 | 75 | 82 |
| 20 | CDEF | 92 | 56 | 76 | 74 | 86 |
| 21 | ACD- | 88 | 66 | 76 | 77 | 78 |
| 22 | CDHI | 86 | 54 | 76 | 74 | 75 |
| 23 | DEFI | 89 | 55 | 76 | 74 | 81 |

TABLE 2C-continued

Patient 2 to 11 Months of Age - Diagnostic Model
Ordered According to Descending Specificity.

Ordered according to descending accuracy

| No | Combination | SEN (%) | SPE (%) | ACC (%) | PPV (%) | NPV (%) |
|---|---|---|---|---|---|---|
| 24 | ADI- | 89 | 54 | 75 | 74 | 83 |
| 25 | ADFI | 85 | 58 | 75 | 74 | 82 |
| 26 | ABFI | 88 | 56 | 75 | 73 | 81 |
| 27 | ADEI | 89 | 55 | 75 | 73 | 83 |
| 28 | BCFH | 88 | 54 | 75 | 73 | 80 |
| 29 | FGHI | 86 | 54 | 74 | 73 | 80 |
| 30 | DFHI | 85 | 53 | 74 | 73 | 0 |
| 31 | CDF- | 92 | 52 | 74 | 74 | 73 |
| 32 | EFGI | 88 | 53 | 74 | 74 | 77 |
| 33 | ABFH | 84 | 59 | 74 | 73 | 78 |
| 34 | ABF- | 86 | 56 | 74 | 72 | 80 |
| 35 | ABCF | 86 | 56 | 74 | 72 | 80 |
| 36 | ABEF | 84 | 59 | 73 | 73 | 79 |
| 37 | ABI- | 91 | 51 | 73 | 72 | 85 |
| 38 | ABCI | 91 | 51 | 73 | 72 | 85 |
| 39 | ACFG | 91 | 50 | 73 | 73 | 77 |
| 40 | AEF- | 89 | 54 | 73 | 72 | 77 |
| 41 | ACDE | 88 | 60 | 73 | 75 | 78 |
| 42 | ACDG | 89 | 53 | 73 | 73 | 72 |
| 43 | DEHI | 77 | 57 | 73 | 73 | 67 |
| 44 | AEFH | 89 | 54 | 73 | 73 | 73 |
| 45 | ADHI | 86 | 51 | 72 | 72 | 79 |
| 46 | BCDF | 87 | 51 | 72 | 72 | 77 |
| 47 | AFHI | 87 | 50 | 72 | 72 | 77 |
| 48 | AFH- | 89 | 50 | 72 | 72 | 71 |
| 49 | ABEI | 88 | 51 | 72 | 71 | 81 |
| 50 | ACDF | 87 | 53 | 71 | 73 | 71 |
| 51 | ABE- | 84 | 57 | 71 | 71 | 78 |
| 52 | ABCE | 84 | 57 | 71 | 71 | 78 |
| 53 | ABC- | 86 | 53 | 70 | 70 | 78 |
| 54 | ABFG | 84 | 52 | 70 | 70 | 76 |
| 55 | ABEG | 81 | 57 | 69 | 70 | 76 |
| 56 | ABEH | 81 | 57 | 69 | 70 | 76 |
| 57 | ABH- | 84 | 53 | 69 | 69 | 76 |
| 58 | ABCH | 84 | 53 | 69 | 69 | 76 |
| 59 | AB-- | 86 | 50 | 69 | 69 | 78 |
| 60 | ABG- | 84 | 54 | 69 | 70 | 77 |
| 61 | ABCG | 81 | 52 | 66 | 69 | 74 |

TABLE 3A

Patient 12 to 60 Months of Age - Diagnostic Model
Ordered According to Descending Sensitivity.

Ordered according to descending sensitivity

| No | Combination | SEN (%) | SPE (%) | ACC (%) | PPV (%) | NPV (%) |
|---|---|---|---|---|---|---|
| 1 | BEF- | 94 | 51 | 81 | 81 | 67 |
| 2 | BFI- | 92 | 51 | 79 | 80 | 71 |
| 3 | BEFI | 92 | 51 | 79 | 80 | 65 |
| 4 | CDF- | 92 | 55 | 81 | 82 | 65 |
| 5 | CDFH | 92 | 50 | 78 | 80 | 65 |
| 6 | BCEF | 91 | 51 | 79 | 81 | 64 |
| 7 | BDEF | 91 | 51 | 79 | 81 | 64 |
| 8 | AD-- | 91 | 60 | 74 | 76 | 71 |
| 9 | ADH- | 91 | 60 | 74 | 76 | 71 |
| 10 | AEF- | 90 | 51 | 74 | 75 | 71 |
| 11 | ACEF | 90 | 51 | 74 | 75 | 71 |
| 12 | CDEI | 89 | 55 | 80 | 80 | 66 |
| 13 | CDFI | 89 | 53 | 79 | 80 | 63 |
| 14 | CDFG | 89 | 55 | 79 | 82 | 63 |
| 15 | ADI- | 89 | 62 | 74 | 78 | 71 |
| 16 | ABCE | 89 | 54 | 74 | 77 | 67 |
| 17 | ABEG | 89 | 53 | 75 | 77 | 67 |
| 18 | ABEH | 89 | 53 | 75 | 77 | 56 |
| 19 | ADGI | 89 | 62 | 74 | 78 | 71 |
| 20 | ADHI | 89 | 62 | 74 | 78 | 67 |

TABLE 3A-continued

Patient 12 to 60 Months of Age - Diagnostic Model Ordered According to Descending Sensitivity.

Ordered according to descending sensitivity

| No | Combination | SEN (%) | SPE (%) | ACC (%) | PPV (%) | NPV (%) |
|---|---|---|---|---|---|---|
| 21 | DFI- | 89 | 54 | 76 | 76 | 67 |
| 22 | ADFI | 89 | 54 | 76 | 76 | 73 |
| 23 | CEFI | 89 | 50 | 79 | 79 | 59 |
| 24 | DEFI | 89 | 50 | 79 | 79 | 57 |
| 25 | ACD- | 89 | 66 | 78 | 81 | 66 |
| 26 | BEFH | 89 | 51 | 78 | 81 | 62 |
| 27 | ACDH | 89 | 72 | 79 | 82 | 70 |
| 28 | AFHI | 89 | 51 | 73 | 76 | 69 |
| 29 | ABC- | 88 | 53 | 71 | 77 | 60 |
| 30 | ABF- | 88 | 58 | 74 | 79 | 73 |
| 31 | ABCD | 88 | 63 | 77 | 82 | 74 |
| 32 | BCDF | 88 | 51 | 76 | 80 | 67 |
| 33 | ABCG | 88 | 55 | 73 | 78 | 60 |
| 34 | ABCH | 88 | 53 | 71 | 77 | 60 |
| 35 | ABCF | 88 | 61 | 76 | 80 | 73 |
| 36 | ABFG | 88 | 58 | 74 | 79 | 73 |
| 37 | AH-- | 88 | 58 | 73 | 75 | 77 |
| 38 | AF-- | 88 | 51 | 73 | 75 | 65 |
| 39 | ADG- | 88 | 56 | 71 | 74 | 69 |
| 40 | AFH- | 88 | 64 | 74 | 77 | 77 |
| 41 | ADGH | 88 | 62 | 74 | 77 | 71 |
| 42 | ADFG | 88 | 50 | 73 | 74 | 69 |
| 43 | ADFH | 88 | 51 | 73 | 75 | 71 |
| 44 | BFGI | 88 | 60 | 78 | 79 | 71 |
| 45 | ABI- | 88 | 75 | 77 | 83 | 76 |
| 46 | CFHI | 88 | 50 | 73 | 75 | 65 |
| 47 | AI-- | 88 | 56 | 70 | 75 | 70 |
| 48 | ACI- | 88 | 54 | 70 | 74 | 74 |
| 49 | AGI- | 88 | 51 | 68 | 74 | 57 |
| 50 | AFI- | 88 | 64 | 73 | 78 | 76 |
| 51 | ABFI | 88 | 80 | 81 | 85 | 78 |
| 52 | ABFH | 88 | 51 | 71 | 76 | 74 |
| 53 | ACDI | 88 | 74 | 78 | 82 | 76 |
| 54 | ACGI | 88 | 51 | 68 | 74 | 57 |
| 55 | ACFI | 88 | 64 | 73 | 78 | 76 |
| 56 | AFGI | 88 | 64 | 73 | 78 | 76 |
| 57 | AEFH | 88 | 51 | 73 | 74 | 69 |
| 58 | CFGI | 87 | 58 | 76 | 77 | 69 |
| 59 | FGHI | 87 | 52 | 73 | 76 | 58 |
| 60 | ABEI | 87 | 60 | 76 | 79 | 63 |
| 61 | AGHI | 87 | 56 | 70 | 75 | 65 |
| 62 | EFI- | 86 | 58 | 81 | 83 | 55 |
| 63 | EFGI | 86 | 58 | 81 | 83 | 55 |
| 64 | ACH- | 86 | 58 | 71 | 75 | 71 |
| 65 | ACF- | 86 | 51 | 71 | 75 | 60 |
| 66 | ACFH | 86 | 64 | 73 | 77 | 73 |
| 67 | ABCI | 86 | 71 | 74 | 80 | 74 |
| 68 | AEFG | 86 | 52 | 73 | 76 | 63 |
| 69 | ABDI | 86 | 71 | 74 | 81 | 70 |
| 70 | ABGI | 86 | 66 | 73 | 79 | 70 |
| 71 | ABGH | 86 | 53 | 69 | 77 | 57 |
| 72 | DFGI | 85 | 57 | 75 | 77 | 64 |
| 73 | AHI- | 85 | 56 | 68 | 75 | 64 |
| 74 | AEFI | 85 | 61 | 75 | 80 | 61 |
| 75 | ACHI | 85 | 56 | 68 | 75 | 64 |
| 76 | ACDE | 84 | 60 | 75 | 81 | 52 |
| 77 | EFHI | 84 | 51 | 77 | 80 | 52 |
| 78 | ACDG | 84 | 72 | 76 | 83 | 65 |
| 79 | ACDF | 84 | 51 | 75 | 80 | 55 |
| 80 | BFHI | 84 | 60 | 75 | 79 | 67 |
| 81 | AG-- | 84 | 60 | 70 | 75 | 69 |
| 82 | ACG- | 84 | 64 | 71 | 77 | 71 |
| 83 | AGH- | 84 | 64 | 71 | 77 | 71 |
| 84 | AFG- | 84 | 66 | 73 | 78 | 71 |
| 85 | ACGH | 84 | 66 | 73 | 78 | 71 |
| 86 | ACFG | 84 | 64 | 71 | 77 | 71 |
| 87 | AFGH | 84 | 64 | 71 | 77 | 71 |
| 88 | ABHI | 83 | 60 | 68 | 76 | 64 |
| 89 | CDEF | 82 | 51 | 73 | 76 | 56 |

TABLE 3B

Patient 12 to 60 Months of Age - Diagnostic Model Ordered According to Descending Specificity.

Ordered according to descending specificity

| No | Combination | SEN (%) | SPE (%) | ACC (%) | PPV (%) | NPV (%) |
|---|---|---|---|---|---|---|
| 1 | ABFI | 88 | 80 | 81 | 85 | 78 |
| 2 | ABI- | 88 | 75 | 77 | 83 | 76 |
| 3 | ACDI | 88 | 74 | 78 | 82 | 76 |
| 4 | ACDH | 89 | 72 | 79 | 82 | 70 |
| 5 | ACDG | 84 | 72 | 76 | 83 | 65 |
| 6 | ABCI | 86 | 71 | 74 | 80 | 74 |
| 7 | ABDI | 86 | 71 | 74 | 81 | 70 |
| 8 | ABGI | 86 | 66 | 73 | 79 | 70 |
| 9 | AFG- | 84 | 66 | 73 | 78 | 71 |
| 10 | ACGH | 84 | 66 | 73 | 78 | 71 |
| 11 | ACD- | 89 | 66 | 78 | 81 | 66 |
| 12 | AFH- | 88 | 64 | 74 | 77 | 77 |
| 13 | AFI- | 88 | 64 | 73 | 78 | 76 |
| 14 | ACFI | 88 | 64 | 73 | 78 | 76 |
| 15 | AFGI | 88 | 64 | 73 | 78 | 76 |
| 16 | ACFH | 86 | 64 | 73 | 77 | 73 |
| 17 | ACG- | 84 | 64 | 71 | 77 | 71 |
| 18 | AGH- | 84 | 64 | 71 | 77 | 71 |
| 19 | ACFG | 84 | 64 | 71 | 77 | 71 |
| 20 | AFGH | 84 | 64 | 71 | 77 | 71 |
| 21 | ABCD | 88 | 63 | 77 | 82 | 74 |
| 22 | ADI- | 89 | 62 | 74 | 78 | 71 |
| 23 | ADGI | 89 | 62 | 74 | 78 | 71 |
| 24 | ADHI | 89 | 62 | 74 | 78 | 67 |
| 25 | ADGH | 88 | 62 | 74 | 77 | 71 |
| 26 | AEFI | 85 | 61 | 75 | 80 | 61 |
| 27 | ABCF | 88 | 61 | 76 | 80 | 73 |
| 28 | AD-- | 91 | 60 | 74 | 76 | 71 |
| 29 | ADH- | 91 | 60 | 74 | 76 | 71 |
| 30 | AG-- | 84 | 60 | 70 | 75 | 69 |
| 31 | ABHI | 83 | 60 | 68 | 76 | 64 |
| 32 | BFGI | 88 | 60 | 78 | 79 | 71 |
| 33 | ABEI | 87 | 60 | 76 | 79 | 63 |
| 34 | ACDE | 84 | 60 | 75 | 81 | 52 |
| 35 | BFHI | 84 | 60 | 75 | 79 | 67 |
| 36 | ABF- | 88 | 58 | 74 | 79 | 73 |
| 37 | ABFG | 88 | 58 | 74 | 79 | 73 |
| 38 | CFGI | 87 | 58 | 76 | 77 | 69 |
| 39 | AH-- | 88 | 58 | 73 | 75 | 77 |
| 40 | ACH- | 86 | 58 | 71 | 75 | 71 |
| 41 | EFI- | 86 | 58 | 81 | 83 | 55 |
| 42 | EFGI | 86 | 58 | 81 | 83 | 55 |
| 43 | DFGI | 85 | 57 | 75 | 77 | 64 |
| 44 | ADG- | 88 | 56 | 71 | 74 | 69 |
| 45 | AI-- | 88 | 56 | 70 | 75 | 70 |
| 46 | AGHI | 87 | 56 | 70 | 75 | 65 |
| 47 | AHI- | 85 | 56 | 68 | 75 | 64 |
| 48 | ACHI | 85 | 56 | 68 | 75 | 64 |
| 49 | CDF- | 92 | 55 | 81 | 82 | 65 |
| 50 | CDEI | 89 | 55 | 80 | 80 | 66 |
| 51 | CDFG | 89 | 55 | 79 | 82 | 63 |
| 52 | ABCG | 88 | 55 | 73 | 78 | 60 |
| 53 | ABCE | 89 | 54 | 74 | 77 | 67 |
| 54 | DFI- | 89 | 54 | 76 | 76 | 67 |
| 55 | ADFI | 89 | 54 | 76 | 76 | 73 |
| 56 | ACI- | 88 | 54 | 70 | 74 | 74 |
| 57 | CDFI | 89 | 53 | 79 | 80 | 63 |
| 58 | ABEG | 89 | 53 | 75 | 77 | 67 |
| 59 | ABEH | 89 | 53 | 75 | 77 | 56 |
| 60 | ABC- | 88 | 53 | 71 | 77 | 60 |
| 61 | ABCH | 88 | 53 | 71 | 77 | 60 |
| 62 | ABGH | 86 | 53 | 69 | 77 | 57 |
| 63 | AEFG | 86 | 52 | 73 | 76 | 63 |
| 64 | FGHI | 87 | 52 | 73 | 76 | 58 |
| 65 | AEF- | 90 | 51 | 74 | 75 | 71 |
| 66 | ACEF | 90 | 51 | 74 | 75 | 71 |
| 67 | AFHI | 89 | 51 | 73 | 76 | 69 |
| 68 | AF-- | 88 | 51 | 73 | 75 | 65 |
| 69 | ADFH | 88 | 51 | 73 | 75 | 71 |
| 70 | AGI- | 88 | 51 | 68 | 74 | 57 |
| 71 | ABFH | 88 | 51 | 71 | 76 | 74 |
| 72 | ACGI | 88 | 51 | 68 | 74 | 57 |

TABLE 3B-continued

Patient 12 to 60 Months of Age - Diagnostic Model
Ordered According to Descending Specificity.

Ordered according to descending specificity

| No | Combination | SEN (%) | SPE (%) | ACC (%) | PPV (%) | NPV (%) |
|---|---|---|---|---|---|---|
| 73 | AEFH | 88 | 51 | 73 | 74 | 69 |
| 74 | ACF- | 86 | 51 | 71 | 75 | 60 |
| 75 | BEF- | 94 | 51 | 81 | 81 | 67 |
| 76 | BFI- | 92 | 51 | 79 | 80 | 71 |
| 77 | BEFI | 92 | 51 | 79 | 80 | 65 |
| 78 | BCEF | 91 | 51 | 79 | 81 | 64 |
| 79 | BDEF | 91 | 51 | 79 | 81 | 64 |
| 80 | BEFH | 89 | 51 | 78 | 81 | 62 |
| 81 | BCDF | 88 | 51 | 76 | 80 | 67 |
| 82 | ACDF | 84 | 51 | 75 | 80 | 55 |
| 83 | CDEF | 82 | 51 | 73 | 76 | 56 |
| 84 | EFHI | 84 | 51 | 77 | 80 | 52 |
| 85 | CDFH | 92 | 50 | 78 | 80 | 65 |
| 86 | CFHI | 88 | 50 | 73 | 75 | 65 |
| 87 | CEFI | 89 | 50 | 79 | 79 | 59 |
| 88 | DEFI | 89 | 50 | 79 | 79 | 57 |
| 89 | ADFG | 88 | 50 | 73 | 74 | 69 |

TABLE 3C

Patient 12 to 60 Months of Age - Diagnostic Model
Ordered According to Descending Accuracy.

Ordered according to descending accuracy

| No | Combination | SEN (%) | SPE (%) | ACC (%) | PPV (%) | NPV (%) |
|---|---|---|---|---|---|---|
| 1 | EFI- | 86 | 58 | 81 | 83 | 55 |
| 2 | EFGI | 86 | 58 | 81 | 83 | 55 |
| 3 | BEF- | 94 | 51 | 81 | 81 | 67 |
| 4 | CDF- | 92 | 55 | 81 | 82 | 65 |
| 5 | ABFI | 88 | 80 | 81 | 85 | 78 |
| 6 | CDEI | 89 | 55 | 80 | 80 | 66 |
| 7 | CEFI | 89 | 50 | 79 | 79 | 59 |
| 8 | DEFI | 89 | 50 | 79 | 79 | 57 |
| 9 | BFI- | 92 | 51 | 79 | 80 | 71 |
| 10 | BEFI | 92 | 51 | 79 | 80 | 65 |
| 11 | BCEF | 91 | 51 | 79 | 81 | 64 |
| 12 | BDEF | 91 | 51 | 79 | 81 | 64 |
| 13 | CDFI | 89 | 53 | 79 | 80 | 63 |
| 14 | CDFG | 89 | 55 | 79 | 82 | 63 |
| 15 | ACDH | 89 | 72 | 79 | 82 | 70 |
| 16 | CDFH | 92 | 50 | 78 | 80 | 65 |
| 17 | ACD- | 89 | 66 | 78 | 81 | 66 |
| 18 | BEFH | 89 | 51 | 78 | 81 | 62 |
| 19 | BFGI | 88 | 60 | 78 | 79 | 71 |
| 20 | ACDI | 88 | 74 | 78 | 82 | 76 |
| 21 | ABCD | 88 | 63 | 77 | 82 | 74 |
| 22 | ABI- | 88 | 75 | 77 | 83 | 76 |
| 23 | EFHI | 84 | 51 | 77 | 80 | 52 |
| 24 | BCDF | 88 | 51 | 76 | 80 | 67 |
| 25 | ABEI | 87 | 60 | 76 | 79 | 63 |
| 26 | ACDG | 84 | 72 | 76 | 83 | 65 |
| 27 | DFI- | 89 | 54 | 76 | 76 | 67 |
| 28 | ADFI | 89 | 54 | 76 | 76 | 73 |
| 29 | ABCF | 88 | 61 | 76 | 80 | 73 |
| 30 | CFGI | 87 | 58 | 76 | 77 | 69 |
| 31 | ABEG | 89 | 53 | 75 | 77 | 67 |
| 32 | ABEH | 89 | 53 | 75 | 77 | 56 |
| 33 | DFGI | 85 | 57 | 75 | 77 | 64 |
| 34 | AEFI | 85 | 61 | 75 | 80 | 61 |
| 35 | ACDE | 84 | 60 | 75 | 81 | 52 |
| 36 | ACDF | 84 | 51 | 75 | 80 | 55 |
| 37 | BFHI | 84 | 60 | 75 | 79 | 67 |
| 38 | AD-- | 91 | 60 | 74 | 76 | 71 |
| 39 | ADH- | 91 | 60 | 74 | 76 | 71 |
| 40 | AEF- | 90 | 51 | 74 | 75 | 71 |
| 41 | ACEF | 90 | 51 | 74 | 75 | 71 |

TABLE 3C-continued

Patient 12 to 60 Months of Age - Diagnostic Model
Ordered According to Descending Accuracy.

Ordered according to descending accuracy

| No | Combination | SEN (%) | SPE (%) | ACC (%) | PPV (%) | NPV (%) |
|---|---|---|---|---|---|---|
| 42 | ADI- | 89 | 62 | 74 | 78 | 71 |
| 43 | ABCE | 89 | 54 | 74 | 77 | 67 |
| 44 | ADGI | 89 | 62 | 74 | 78 | 71 |
| 45 | ADHI | 89 | 62 | 74 | 78 | 67 |
| 46 | ABF- | 88 | 58 | 74 | 79 | 73 |
| 47 | ABFG | 88 | 58 | 74 | 79 | 73 |
| 48 | AFH- | 88 | 64 | 74 | 77 | 77 |
| 49 | ADGH | 88 | 62 | 74 | 77 | 71 |
| 50 | ABCI | 86 | 71 | 74 | 80 | 74 |
| 51 | ABDI | 86 | 71 | 74 | 81 | 70 |
| 52 | CFHI | 88 | 50 | 73 | 75 | 65 |
| 53 | FGHI | 87 | 52 | 73 | 76 | 58 |
| 54 | CDEF | 82 | 51 | 73 | 76 | 56 |
| 55 | AFHI | 89 | 51 | 73 | 76 | 69 |
| 56 | AH-- | 88 | 58 | 73 | 75 | 77 |
| 57 | AF-- | 88 | 51 | 73 | 75 | 65 |
| 58 | ADFG | 88 | 50 | 73 | 74 | 69 |
| 59 | ADFH | 88 | 51 | 73 | 75 | 71 |
| 60 | AFI- | 88 | 64 | 73 | 78 | 76 |
| 61 | ACFI | 88 | 64 | 73 | 78 | 76 |
| 62 | AFGI | 88 | 64 | 73 | 78 | 76 |
| 63 | AEFH | 88 | 51 | 73 | 74 | 69 |
| 64 | ACFH | 86 | 64 | 73 | 77 | 73 |
| 65 | AEFG | 86 | 52 | 73 | 76 | 63 |
| 66 | ABGI | 86 | 66 | 73 | 79 | 70 |
| 67 | AFG- | 84 | 66 | 73 | 78 | 71 |
| 68 | ACGH | 84 | 66 | 73 | 78 | 71 |
| 69 | ABCG | 88 | 55 | 73 | 78 | 60 |
| 70 | ADG- | 88 | 56 | 71 | 74 | 69 |
| 71 | ABFH | 88 | 51 | 71 | 76 | 74 |
| 72 | ACH- | 86 | 58 | 71 | 75 | 71 |
| 73 | ACF- | 86 | 51 | 71 | 75 | 60 |
| 74 | ACG- | 84 | 64 | 71 | 77 | 71 |
| 75 | AGH- | 84 | 64 | 71 | 77 | 71 |
| 76 | ACFG | 84 | 64 | 71 | 77 | 71 |
| 77 | AFGH | 84 | 64 | 71 | 77 | 71 |
| 78 | ABC- | 88 | 53 | 71 | 77 | 60 |
| 79 | ABCH | 88 | 53 | 71 | 77 | 60 |
| 80 | AI-- | 88 | 56 | 70 | 75 | 70 |
| 81 | ACI- | 88 | 54 | 70 | 74 | 74 |
| 82 | AGHI | 87 | 56 | 70 | 75 | 65 |
| 83 | AG-- | 84 | 60 | 70 | 75 | 69 |
| 84 | ABGH | 86 | 53 | 69 | 77 | 57 |
| 85 | AGI- | 88 | 51 | 68 | 74 | 57 |
| 86 | ACGI | 88 | 51 | 68 | 74 | 57 |
| 87 | AHI- | 85 | 56 | 68 | 75 | 64 |
| 88 | ACHI | 85 | 56 | 68 | 75 | 64 |
| 89 | ABHI | 83 | 60 | 68 | 76 | 64 |

It will be noted in the above tables that a maximum of four diagnostic parameters are used in combination. This is because the Inventors research has surprisingly indicated that using a combination of more than four diagnostic features increases computational complexity without any substantial diagnostic performance gain.

If the clinician picks "accuracy" optimization then the best model will be the top row of Table A3 (if the patient is 2 to 11 months of age) and top Row of Table B3 (if the patient is 12 to 60 months of age). However, if the parameters that were entered by the clinician do not allow for the top row #1 to be used then the microprocessor will check if row #2 can be used and so on. Since the parameters that are listed (among the nine set out in table 1B) are common measurements usually it is not necessary to descend far down the rows to find a first usable model.

For example,

Table 2B: 2-11 months: parameters:
1 ACDI (breathing rate, runny nose, # days with runny nose, oxygen saturation)»Sens 91%, spec 70%.
13 ABCD (breathing rate, fever, runny nose, # days with runny nose)»sens 91%, spec 61% etc.

Figure 8:
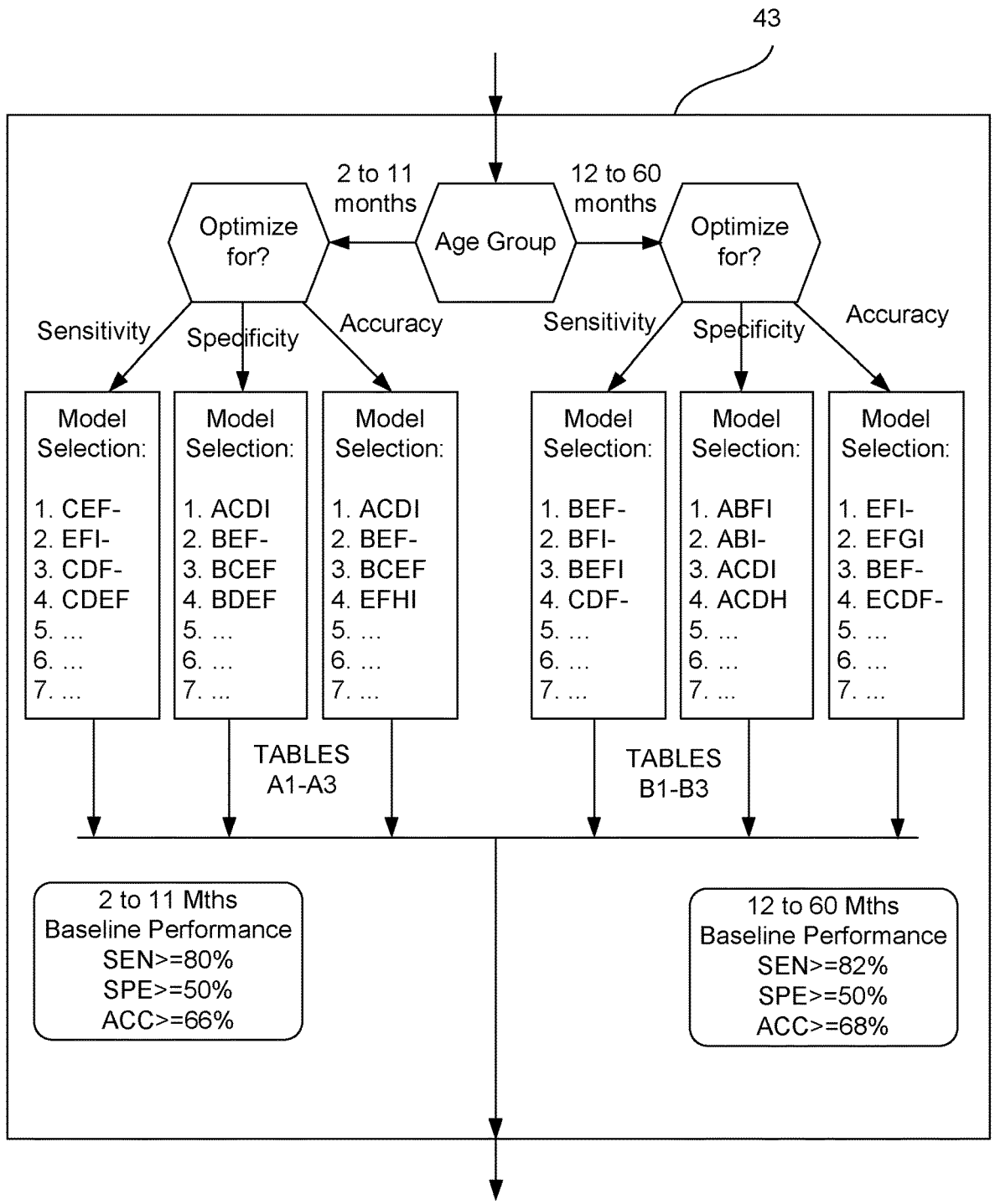
FIG. 8 is a flowchart illustrating a diagnostic model selection procedure by the diagnostic device at box 43 of the flowchart of FIG. 2.
Figure 9:
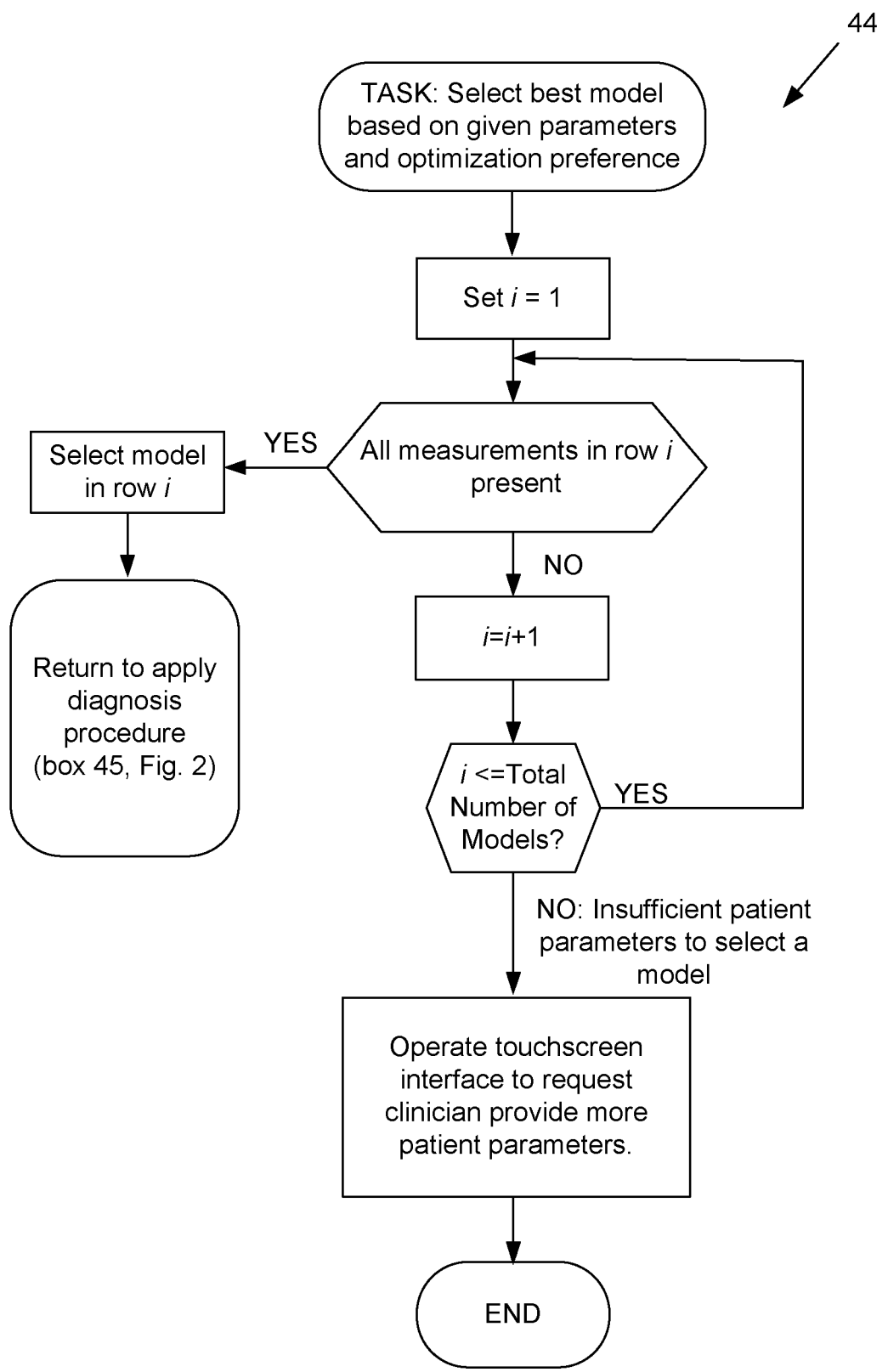
FIG. 9 is a flowchart illustrating a procedure of the diagnostic device during selection of the best diagnostic model.

The flowchart of FIG. 8 details the model selection process that microprocessor 3 performs under control of diagnostic application 6, within box 43 of the flowchart of FIG. 2. Using the data for tables A1-A3 or B1-B3 (depending on age), the clinician's inputted preference for optimization for sensitivity, specificity or accuracy, and the inputted patient parameters, the device 1 automatically selects a particular numbered diagnostic model using the procedure set out in FIG. 9.

Figure 10:
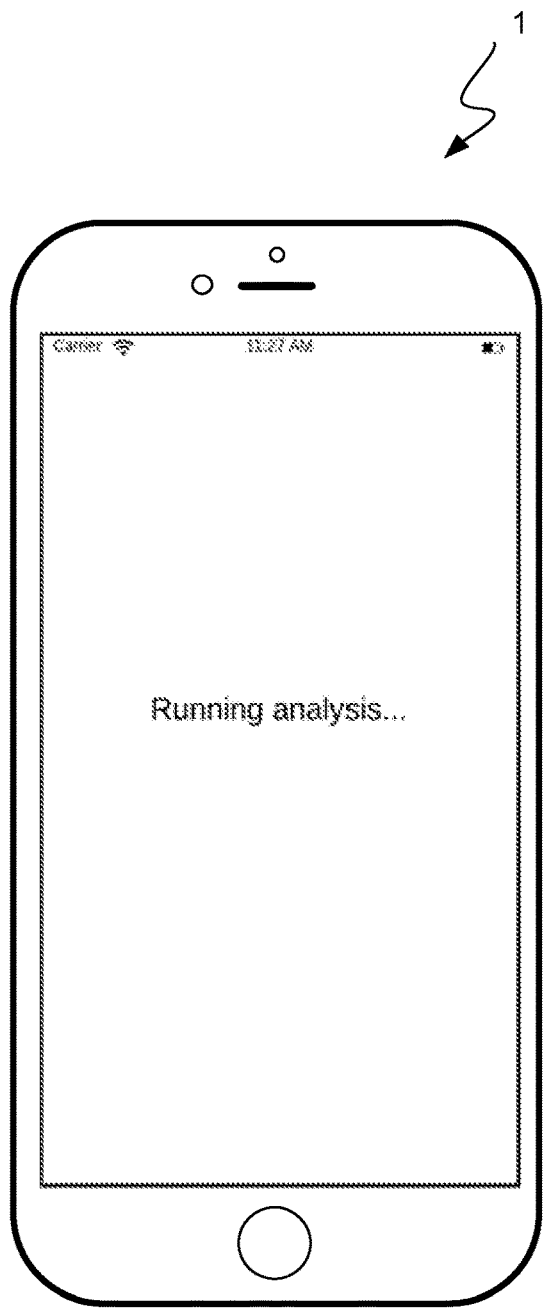
FIG. 10 depicts a screen generated by the diagnostic device whilst it is analyzing the diagnostic information.

At box 45 (FIG. 2) the patient values that were entered for each of the diagnostic parameters that were selected are applied by microprocessor 3 to the selected optimal diagnostic model. The screen that is depicted in FIG. 10 is presented on LCD touchscreen interface 11 whilst this process runs.

Figure 11:
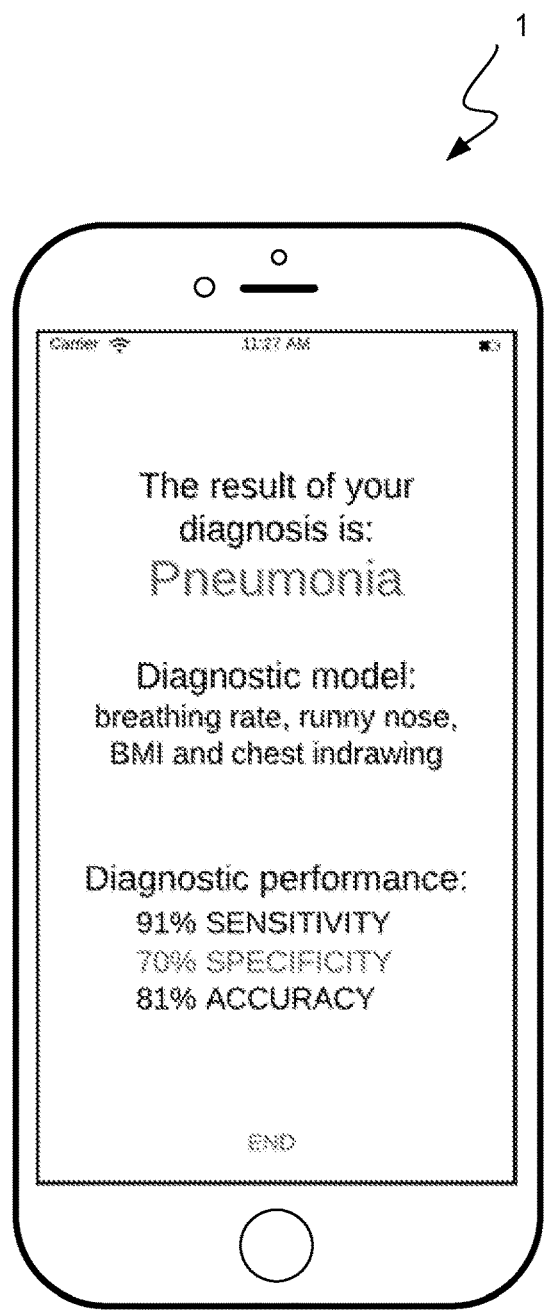
FIG. 11 depicts a screen generated by the diagnostic device presenting the results of the analysis to the clinician.

At box 47 microprocessor 3 operating under control of the diagnostic application 6 operates the LCD touchscreen interface 11 to present the diagnostic results to the carer as shown in the screen of FIG. 11.

Returning to the flowchart of FIG. 2, at box 49 the microprocessor 3 may save the diagnosis results either locally to memory 5 or externally via WAN/WLAN interface and antenna 29 to cloud server 33 via data network 31. At box 50, if the diagnostic results indicate a disease state such as pneumonia then the carer may use that information, as indicated in box 52, to apply therapy to the patient 2, for example by organising hospitalisation and/or providing antibiotics or antiviral medication. The clinician 4 may then indicate, at box 55, a desire to diagnose another patient in which case the procedure is repeated in respect of another patient.

As will be explained in the Appendices of this specification, the Inventors developed the diagnostic models from quantitative test data derived from a population of subjects including patients suffering from respiratory disease. The various models are arranged to classify a patient as "diseased" or "non-diseased" based upon the diagnostic parameters for the patient that are entered by the clinician. A preferred approach to developing the models is by use of a logistic regression machine (LRM). Other types of classification decision engines may also be used, for example support vector machines (SVMs).

As explained in Section 1.2.2 of Appendix A herein, the use of cough sound features from just one or two coughs of a patient has been found by the Inventors to provide a significant diagnosis performance gain. Where it is possible to record a cough sound from patient 2 by means of microphone 25, those sounds can be processed by a cough feature extraction and processed along with other diagnostic parameters by a suitable one of the diagnostic models 20.

Figure 11A:
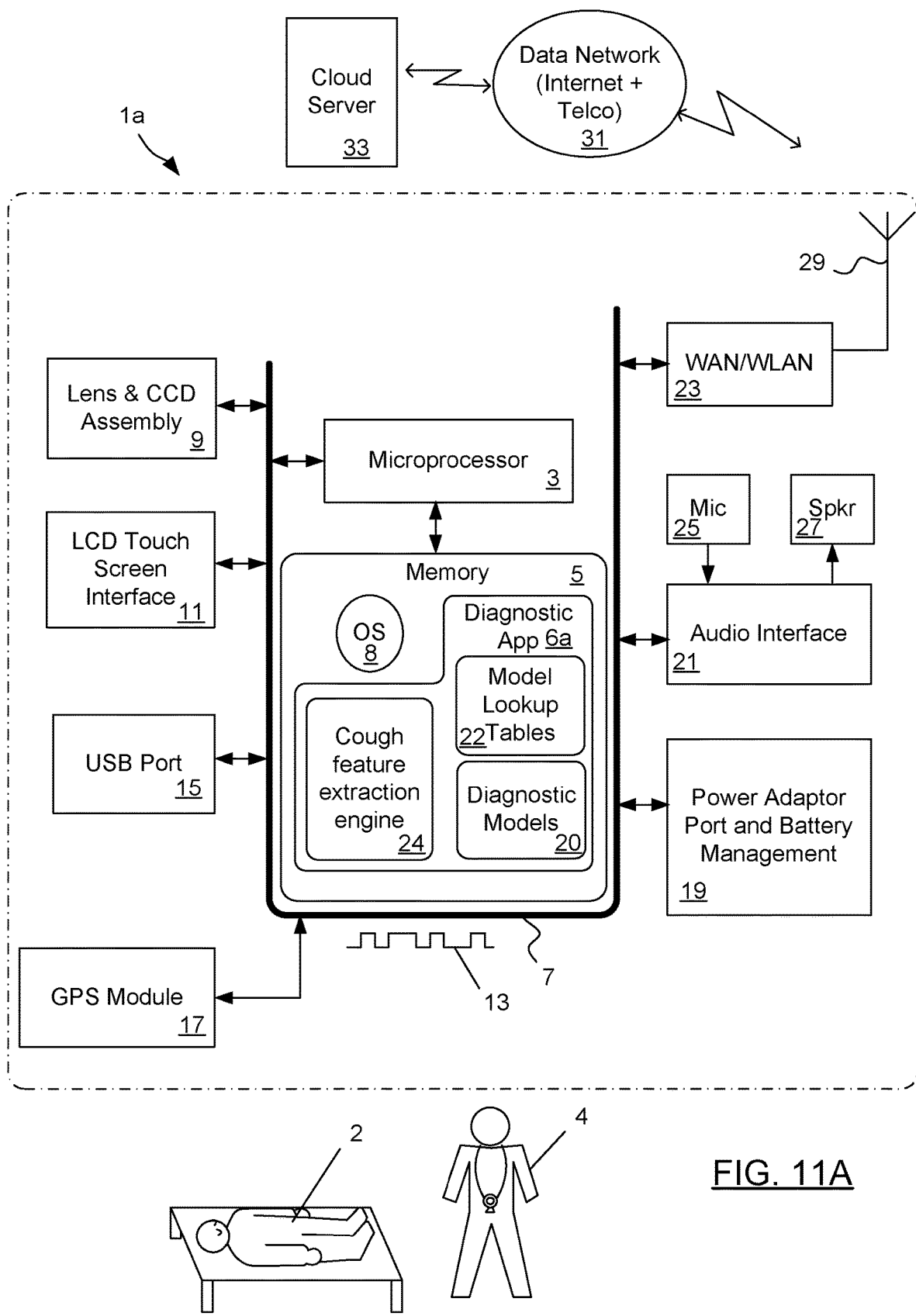
FIG. 11A is a block diagram of a diagnostic device according to a further embodiment of the present invention which is arranged to take into account cough sounds of the patient.

Referring now to FIG. 11A, there is shown a further embodiment of the invention comprising diagnostic device 1a, which as far as hardware is concerned is the same as previously described diagnostic device 1, programmed with a variation of the diagnostic application 6 that was previously discussed being diagnostic application 6a. Diagnostic application 6a includes a cough feature extraction engine 24. The cough feature extraction engine 24 includes instructions for the microprocessor 3 to analyse a cough sound from the patient 2 that is received via microphone 25 and audio interface 21 and to generate corresponding cough features.

Cough feature extraction is known in the prior art and is described for example in international patent publication No. WO 2013/142908 by present Inventor Abeyratne et al., the disclosure of which is hereby incorporated by reference in its entirety.

Microprocessor 3 applies the cough features to diagnostic models 20 that form part of the diagnostic application 6a and which are configured to take into account other diagnostic parameter values that are input by the clinician 4. This is done by adding cough features as a grouped-features to the existing lookup tables set out as Tables 2A-3C. The modified tables including the cough sounds are arranged with the models in decreasing performance as before. Users, e.g. clinician 4, can select the cough sounds as a measurement in the event that they are able to collect sounds from patient 2. Otherwise they do not elect that option, just as in the case of other clinical signs. Then following the same logic as discussed previously with respect to Tables 2A-3C the diagnostic device 1 is programmed by means of diagnostic application 6 to pick the best model corresponding to the available measurements.

Figure 11B:
Figure 11C:
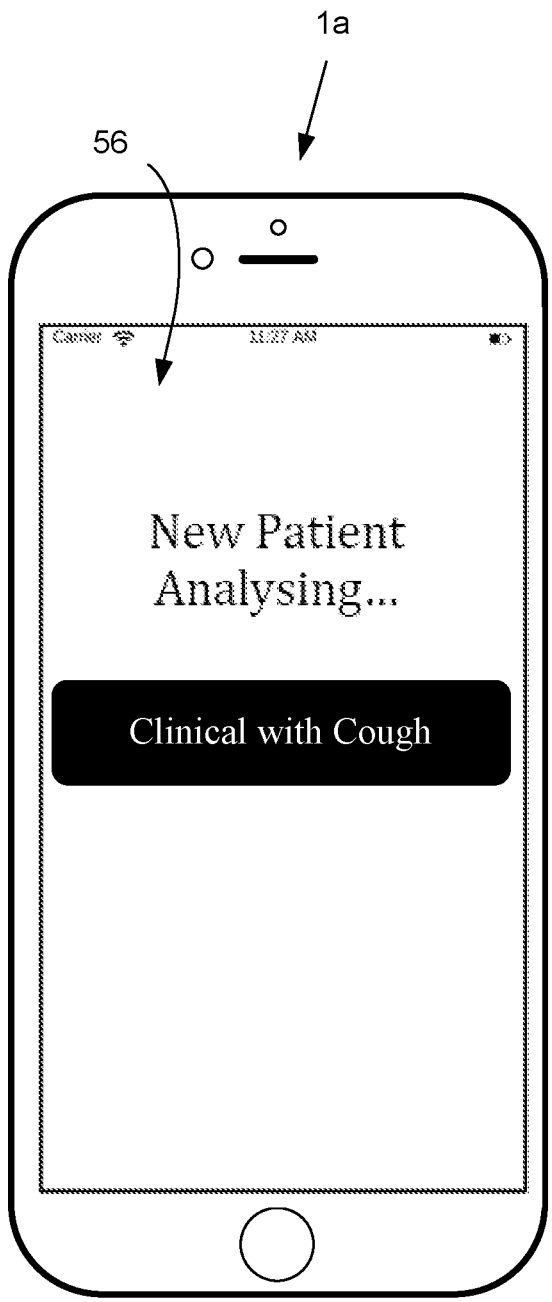
Figure 11D:
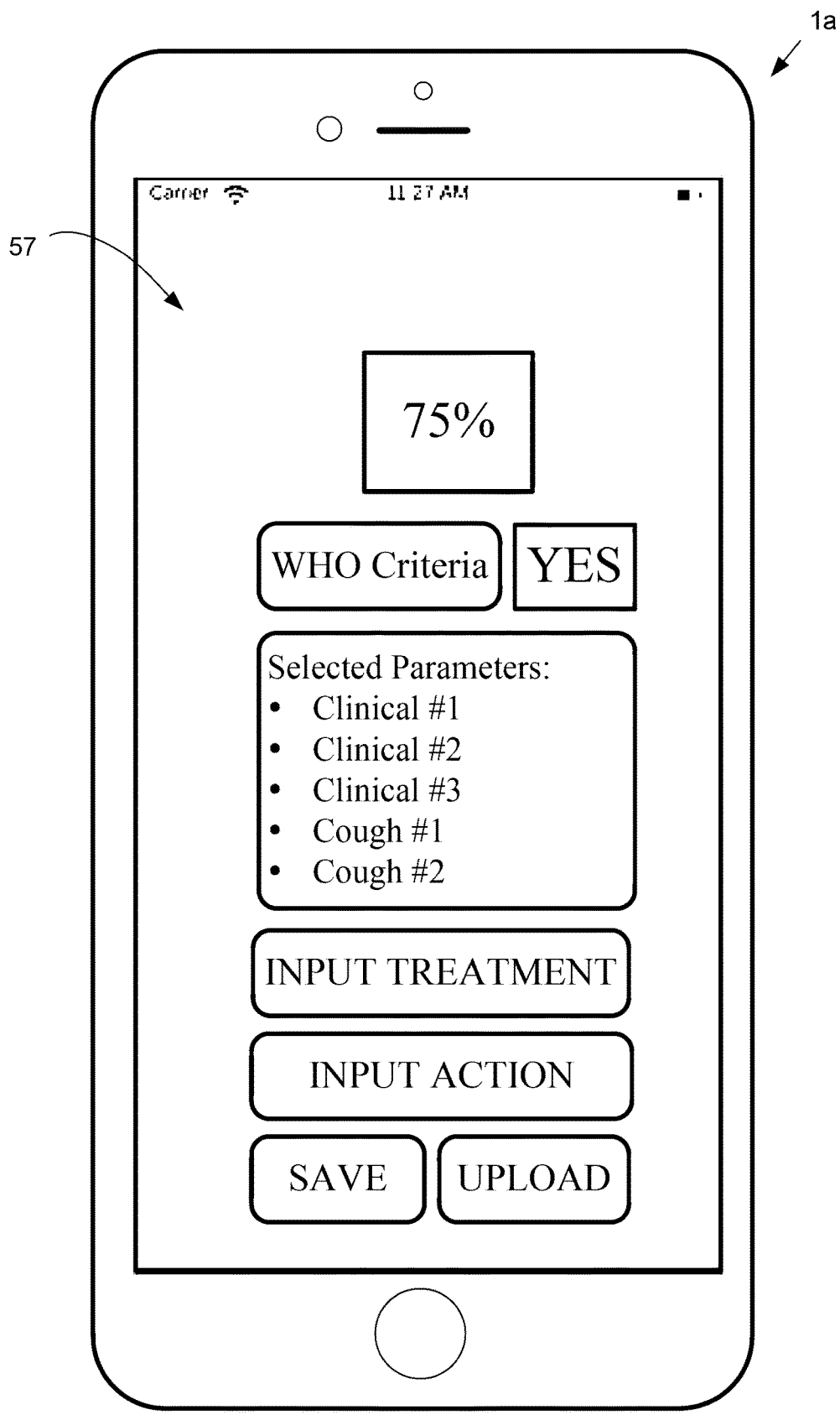

FIGS. 11B and 11C depict screens 54, 56 that are generated on LCD touchscreen interface 11 by the microprocessor 3 under control of the diagnostic application 6 to prompt for the clinician 4 to capture at least two cough sound samples from the patient 2. FIG. 11D depicts a screen 57 that the microprocessor 3 generates on interface 11 for presenting the results of the analysis to the clinician 4. As discussed in Appendix A, in other embodiments only a single cough sound has been found to assist in improving the performance of the machine diagnosis.

APPENDIX A

Childhood Pneumonia Diagnosis Using Clinical and Cough Features 1.1 Materials and Method
1.1.1 Study Population A total of 222 children were recruited during the data collection: 93 females and 129 males with a median age of 9 months and an inter-quartile range (IQR) of 4.25-20 months. Due to the absence of one or more of the required parameters, we excluded 123 patients from further consideration, leaving 99 children with complete data. The distribution of the 99 children is a close representation of the initial 222 children recruited, as shown in Table 4.1. There were 52 children aged 2-11 months and 47 aged 12-60 months. Of the 99 children, 67 were pneumonia positive, whereas the remaining 32 experienced a mix of asthma, bronchitis, bronchiolitis, heart disease, malnutrition, wheezing, etc. The non-pneumonia patients are the control set for this study.

TABLE 4.1

Children representation between initial recruitment and actual number in study

| Category | Initial Recruitment (n = 222) | Model Building (n = 99) |
|---|---|---|
| Age | | |
| Median | 10 months | 11 months |
| IQR | 17 months | 6 months |
| Diagnosis Ratio | 2.47:1 | 2.1:1 |
| Pneumonia | 158 patients | 67 patients |

TABLE 4.1-continued

Children representation between initial recruitment and actual number in study

| Category | Initial Recruitment (n = 222) | Model Building (n = 99) |
|---|---|---|
| Non-Pneumonia | 64 patients | 32 patients |
| Gender Ratio (M/F) | 1.39:1 | 1.3:1 |
| Male | 128 patients | 56 patients |
| Female | 92 patients | 43 patients |
| Age Group | | |
| <2 Months | 13 subjects | 0 subjects |
| 2-11 Months | 109 subjects | 52 subjects |
| 12-60 Months | 100 subjects | 47 subjects |

1.1.2 Analysis of Data

Figure 12:
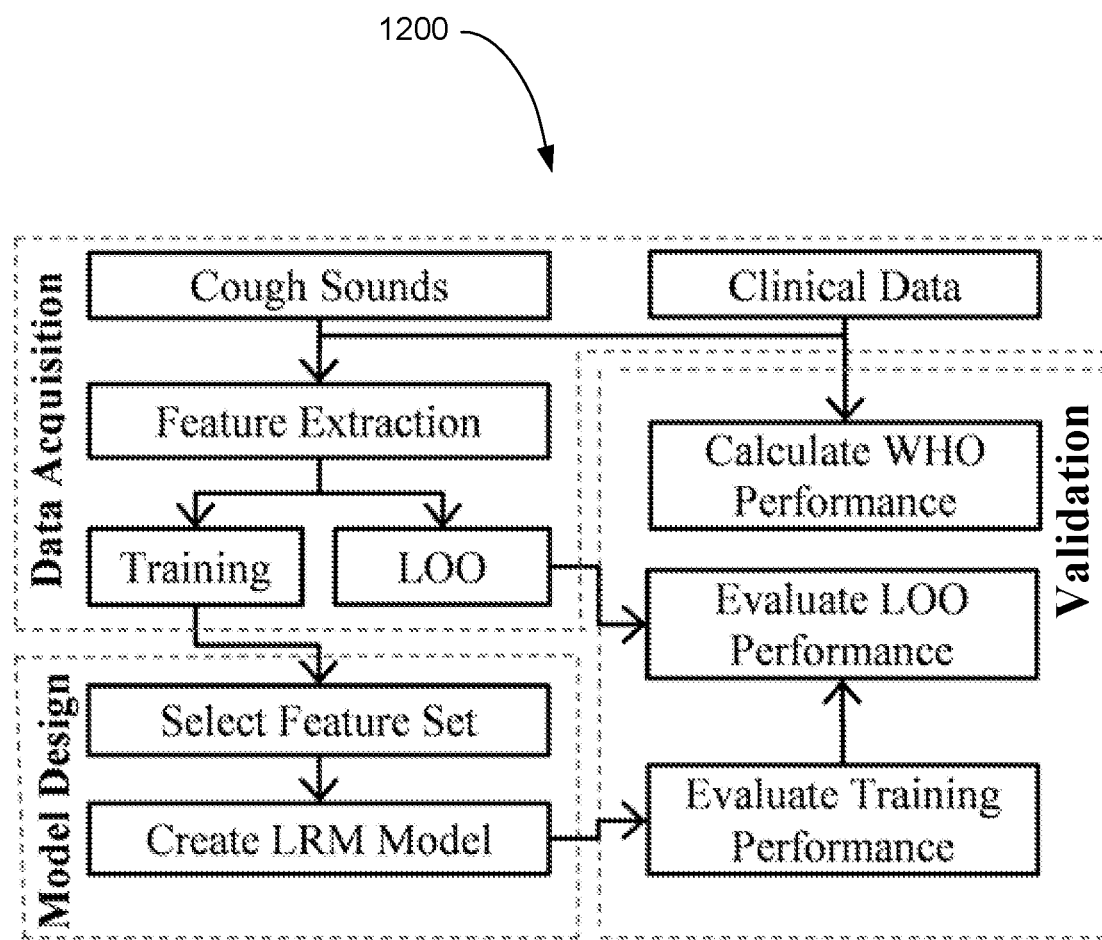
FIG. 12 is a flow diagram detailing the process used to analyse cough sound data for designing a diagnostic model for use in an embodiment of the present invention.

The flow diagram 1200 presented in FIG. 12 details the process used in analysing our data. For analysis, the dataset is split into two age groups, 2-11 months and 12-60 months. This follows the WHO/IMCI procedure which applies different breathing rate thresholds for each age group. Clinical and cough features from each group are tabled into a feature matrix for processing.

An LRM classifier was used to train a model for each feature combination. This technique creates a non-linear model based on the feature parameters and applies different weights to each parameter. The LRM training process adjusts the weights such that each model is adapted to differentiate pneumonia patients from non-pneumonia patients. We exhaustively analysed feature combinations from one up to six features at a time. The process was divided into several phases: clinical features only, clinical plus cough features from one cough, and clinical plus cough features from two coughs. Cough features from multiple coughs were averaged to a single set prior to analysis.

Leave one out (LOO) cross-validation was used to validate the results. At each iteration, one patient was designated the LOO person and the rest became training set. An LRM model was created based on the training set and the cut-off threshold, carefully selected such that Sn≥90% with Sp as high as possible. The model parameters were then fixed and used to evaluate the training set and LOO individual. Applying the trained model on the training set provides the training performance such that the LOO person is classified using the trained model. On the next iteration, another individual is designated LOO whilst the others become the training set. At the end of the iteration process where every patient has been designated once as an LOO individual, the procedure performance was calculated.

1.2 Results

In this section, we show the results of our analysis in three phases. Firstly, we compare the WHO/IMCI procedure performance in each age group with clinical features only. This is followed by comparison with clinical features plus features from one cough. Lastly, we compare the WHO/IMCI procedure results with our procedure using clinical plus cough features from two coughs.

1.2.1 Clinical Only Features

The results in Table 4.2 show the WHO/IMCI classification and our procedure performance using only clinical features for each age group. The WHO/IMCI procedure performed with an Sn and Sp of 91.2% and 26.7%, respectively, for the 2-11 month age group. In the older age group, the corresponding Sn and Sp are 83.3% and 11.8%. The best model in the 2-11 month age group, using clinical features only, demonstrated an Sn and Sp of 86.5% and 60.0%, respectively, using fever, days with cough, temperature and heart rate. In the 12-60 month age group, the best model identified used fever, temperature, runny nose and heart rate, with an Sn and Sp of 90.0% and 76.6%, accordingly.

1.2.2 Clinical Plus One Cough

When features from just one cough were added to the mix, there was significant performance gain. For the 2-11 month age group, the best model showed an Sn and Sp of 89.2% & 73.3%, respectively. This Sp value is the equivalent of 275% that of the WHO/IMCI procedure with only a small drop in the Sn. The numbers can be seen in Table 4.3. For the 12-60 month age group, the best model using clinical features and one cough performed with an Sn and Sp of 90.0% & 82.4%, respectively. Compared to the WHO/IMCI performance, the Sp is equivalent to 82.4/11.8=698% and the Sn is slightly higher than the WHO/IMCI's.

TABLE 4.2

Performance comparison between WHO and clinical feature combinations
Classification Performance (%)

| | $S_n$ | $S_p$ | $A_{cc}$ | PPV | NPV |
|---|---|---|---|---|---|
| 2-11 Months | | | | | |
| WHO | 91.2 | 26.7 | 73.1 | 75.6 | 57.1 |
| Fever + Days with cough + Temperature + Heart rate | | | | | |
| Training | 91.7 | 64.9 | 84.0 | 86.6 | 76.0 |
| LOO | 86.5 | 60.0 | 78.8 | 84.2 | 64.3 |
| Days with cough + Breathing rate + Temperature + Days with runny nose | | | | | |
| Training | 91.9 | 60.2 | 82.8 | 85.1 | 75.0 |
| LOO | 86.5 | 53.3 | 76.9 | 82.1 | 61.5 |
| Fever + Days with cough + Runny nose + Heart rate | | | | | |
| Training | 92.3 | 33.8 | 75.4 | 77.5 | 64.0 |
| LOO | 89.2 | 33.3 | 73.1 | 76.7 | 55.6 |
| 12-60 Months | | | | | |
| WHO | 83.3 | 11.8 | 57.5 | 62.5 | 28.6 |
| Fever + Temperature + Runny nose + Heart rate | | | | | |
| Training | 92.0 | 67.9 | 83.2 | 83.5 | 82.8 |
| LOO | 90.0 | 70.6 | 83.0 | 84.4 | 80.0 |
| Fever + Days with cough + Temperature + Heart rate | | | | | |
| Training | 92.1 | 68.5 | 83.5 | 83.8 | 83.0 |
| LOO | 86.7 | 70.6 | 80.9 | 83.9 | 75.0 |
| Breathing rate + Temperature + Runny nose + Days with runny nose | | | | | |
| Training | 92.1 | 51.3 | 77.2 | 77.3 | 77.7 |
| LOO | 86.7 | 70.6 | 80.9 | 83.9 | 75.0 |

*LOO = leave one out, $S_n$ = sensitivity, $S_p$ = Specificity, $A_{cc}$ = accuracy, PPV = positive predictive value, NPV = negative predictive value

TABLE 4.3

Performance comparison between WHO and clinical plus one cough feature combinations
Classification Performance (%)

| | $S_n$ | $S_p$ | $A_{cc}$ | PPV | NPV |
|---|---|---|---|---|---|
| 2-11 Months | | | | | |
| WHO | 91.2 | 26.7 | 73.1 | 75.6 | 57.1 |
| Days with cough + Temperature + Days with runny nose + 1 cough | | | | | |
| Training | 91.7 | 79.7 | 88.3 | 91.8 | 79.6 |
| LOO | 89.2 | 73.3 | 84.6 | 89.2 | 73.3 |

TABLE 4.3-continued

Performance comparison between WHO and clinical
plus one cough feature combinations
Classification Performance (%)

| | $S_n$ | $S_p$ | $A_{cc}$ | PPV | NPV |
|---|---|---|---|---|---|
| Fever + Days with cough + 1 cough | | | | | |
| Training | 91.7 | 66.7 | 84.5 | 87.2 | 76.6 |
| LOO | 89.2 | 66.7 | 82.7 | 86.8 | 71.4 |
| Days with cough + Breathing rate + Temperature + 1 cough | | | | | |
| Training | 92.1 | 61.4 | 83.2 | 85.5 | 75.8 |
| LOO | 89.2 | 60.0 | 80.8 | 84.6 | 69.2 |
| 12-60 Months | | | | | |
| WHO | 83.3 | 11.8 | 57.5 | 62.5 | 28.6 |
| Temperature + Runny nose + Heart rate + 1 cough | | | | | |
| Training | 92.0 | 82.2 | 88.4 | 90.1 | 85.3 |
| LOO | 90.0 | 82.4 | 87.2 | 90.0 | 82.4 |
| Breathing rate + Days with runny nose + 1 cough | | | | | |
| Training | 92.0 | 64.7 | 82.0 | 82.6 | 81.8 |
| LOO | 86.7 | 82.4 | 85.1 | 89.7 | 77.8 |
| Fever + Runny nose + 1 cough | | | | | |
| Training | 92.1 | 43.3 | 74.4 | 74.3 | 75.6 |
| LOO | 90.0 | 52.9 | 76.6 | 77.1 | 75.0 |

*LOO = leave one out, $S_n$ = sensitivity, $S_p$ = specificity, $A_{cc}$ = accuracy, PPV = positive predictive value, NPV = negative predictive value

TABLE 4.4

Performance comparison between WHO and clinical
plus two coughs feature combinations
Classification Performance (%)

| | $S_n$ | $S_p$ | $A_{cc}$ | PPV | NPV |
|---|---|---|---|---|---|
| 2-11 Months | | | | | |
| WHO | 91.2 | 26.7 | 73.1 | 75.6 | 57.1 |
| Days with cough + Breathing rate + Temperature + 2 coughs | | | | | |
| Training | 91.8 | 85.7 | 90.0 | 94.1 | 80.9 |
| LOO | 89.2 | 86.7 | 88.5 | 94.3 | 76.5 |
| Days with cough + 2 coughs | | | | | |
| Training | 91.7 | 80.5 | 88.5 | 92.1 | 79.8 |
| LOO | 89.2 | 80.0 | 86.5 | 91.7 | 75.0 |
| Fever + Days with cough + Breathing rate + Days with runny nose + 2 coughs | | | | | |
| Training | 91.7 | 86.4 | 90.2 | 94.3 | 80.9 |
| LOO | 86.5 | 80.0 | 84.6 | 91.4 | 70.6 |
| 12-60 Months | | | | | |
| WHO | 83.3 | 11.8 | 57.5 | 62.5 | 28.6 |
| Breathing rate + Temperature + Heart rate + 2 coughs | | | | | |
| Training | 92.1 | 83.7 | 89.0 | 90.9 | 85.7 |
| LOO | 90.0 | 88.2 | 89.4 | 93.1 | 83.3 |
| Fever + Runny nose + O2 Saturation + 2 coughs | | | | | |
| Training | 92.0 | 74.5 | 85.6 | 86.5 | 84.1 |
| LOO | 90.0 | 76.5 | 85.1 | 87.1 | 81.3 |
| Fever + Runny nose + BMI + 2 coughs | | | | | |
| Training | 92.1 | 69.4 | 83.8 | 84.3 | 83.4 |
| LOO | 90.0 | 70.6 | 83.0 | 84.4 | 80.0 |

*LOO = leave one out, $S_n$ = sensitivity, $S_p$ = specificity, $A_{cc}$ = accuracy, PPV = positive predictive value, NPV = negative predictive value 1.2.3 Clinical Plus Two Coughs Table 4.4 shows the LRM performance when clinical features are combined with features from two coughs. The best model for the 2-11 month age group utilises days with cough, breathing rate and temperature along with the cough features. This results in Sn and Sp of 89.2% and 86.7%, respectively. The Sp is equivalent to 325% that of the WHO/IMCI procedure. In the 12-60 month age group, the best LRM model uses breathing rate, temperature and heart rate along with cough features. The model performance was 90.0% Sn and 88.2% Sp. The Sp in this case is equivalent to 747% of the WHO/IMCI counterpart.

1.3 Discussion

The aim in this study was to investigate the use of common clinical parameters in conjunction with cough sound analysis to diagnose childhood pneumonia. A key requirement for this objective is to perform better than the WHO/IMCI procedure. Our results have shown that adding cough sound analysis indeed helps identify childhood pneumonia better than just relying on clinical parameters. In this study, the WHO/IMCI procedure performed with an Sn and Sp range of 83-91% and 12-27%, respectively. Our best performing models with two cough sounds were able to classify pneumonia with an Sn and Sp range of 89-90% and 87-88%, respectively. These are the results from the LOO validation.

Cough is one of the most common symptoms in children with respiratory problems. The WHO/IMCI procedure takes into account the existence of cough but does not utilise it fully. Our method extracts the important features from cough sound recordings and uses them to augment our clinically based features in diagnosing pneumonia. We have shown this to provide the best performance compared to using cough sounds or clinical features only.

The field of cough sound analysis is still relatively untouched, despite the recent advancement in technology. We believe cough contains much more information regarding the physiology of the lung compared to what is currently known. A diseased lung hypothetically could change the physical characteristics of the lung and the characteristic sound of cough in a way specific to the disease. In the case of childhood pneumonia, we have shown in our previous studies that cough is a feasible parameter to use for diagnosis [7, 62]. The number of coughs used there was 15 per person, much higher that what has been used in this thesis. We now have shown that, combined with clinical parameters, much fewer cough sounds are potentially required in order to produce an accurate diagnosis.

1.4 Conclusion

We have demonstrated the potential benefits of combining clinical and cough features for childhood pneumonia diagnosis in resource-poor regions. The models we developed exhibited sensitivities of ~90% and specificities in the range of 325-747% times the WHO/IMCI procedure. The key parameters that worked best were the combination of breathing rate, temperature, heart rate and cough sound analysis. The clinical features are easily measurable and in the absence of key parameters, we could switch to other models and they can still perform well.

It should be noted that this study is currently based on a relatively small number of subjects (n=99) and there is yet to be established a gold standard for pneumonia diagnosis. The reference standard we used stems from a combination of clinical diagnosis by paediatricians aided by auscultations, laboratory analysis, chest x-ray (where applicable) and the subject's response to treatment over the clinical course of the disease.

End of Appendix A

APPENDIX B

Exhaustive Mathematical Analysis of Simple Clinical Measurements

In 1990, the World Health Organization (WHO) and UNICEF proposed the WHO criteria for childhood pneumonia classification in resource-poor regions. This is the current de facto diagnostic method used by community health workers in resource limited settings as a rapid low cost alternative in frontline health facilities. Table 5 shows the WHO/IMCI guideline for pneumonia classification in resource poor regions.

TABLE 5

WHO/IMCI guidelines for pneumonia classification in resource-poor regions [35, 36]

| Sequence for Criteria Application | Classification |
| --- | --- |
| 1. History of cough and/or difficult breathing of less than 3 weeks duration | Screened in for next procedure |
| 2. Increased respiratory rate (tachypnea): ≥60/min if age <2 months, ≥50/min if age 2-11 months, ≥40/min if age 12-60 months | Non-severe pneumonia |
| 3. Lower chest wall indrawing | Severe pneumonia |
| 4. Cyanosis or inability to feed or drink | Very severe pneumonia |

The WHO/IMCI guideline dictates that if a patient exhibits symptoms of cough/breathing difficulty, the patient is screened for the next step.

Breathing rate is taken and if it exceeds the limit (50 breaths per minute (bpm) for age 2-11 months, 40 bpm for age 12-60 months), non-severe pneumonia is declared. Danger signs such as lower chest indrawing and inability to feed or drink would put the patient in the severe pneumonia category requiring immediate attention.

Researchers have generally recognized the limitations of the WHO criteria, which are sensitive but not very specific[9,15,16]. Over the years, others have suggested the addition of fever[17], grunting and nasal flaring[8], temperature and oxygen saturation[18]. Rambaud-Althaus et al. proposed a combination of signs in a decision tree format to improve clinical diagnosis accuracy[8]. Pneumonia Etiology Research for Child Health (PERCH) investigators developed their own standard interpretations of the symptoms and signs based on the WHO criteria for a clinical case definition of pneumonia[16].

All these approaches make important contributions to dealing with the global burden of pneumonia, but largely suffer from the same type of limitations afflicting the WHO criteria for resource-poor regions. These methods also rely on health workers to perform measurements and interpret data using basic binary decisions around fixed thresholds.

Methods

Study Organization

The clinical data used for this study were collected by the Gadjah Mada University-Sardjito Hospital, Yogyakarta, Indonesia, in partnership with The University of Queensland, Brisbane, Australia. The data collection began in December 2010 and continued until March 2014. The ethics committees of the Sardjito Hospital and The University of Queensland approved the study protocol. The inclusion/exclusion criteria are given in Table 6 (Supplementary) below:

TABLE 6

Patient Recruitment Criteria

| Inclusion criteria | Exclusion criteria |
| --- | --- |
| Patients with symptoms of chest infection. At least 2 of: Cough Sputum Increased breathlessness Temperature >37.5° C. Consent from parent/guardian | Advanced disease where recovery is not expected e.g. Terminal lung cancer Droplet precautions NIV required No informed-consent |

Patients are included if they exhibit any 2 symptoms of cough, sputum, increased breathlessness and temperature >37.5° C. Parental consent was sought prior to inclusion if the patient met the criteria and excluded if consent was not granted. Exclusion criteria also applied to patients showing symptoms of advanced disease, terminal lung cancer and/or requiring a nasal drip IV, as these may skew the outcomes. As a precaution, patients showing droplet-spread disease were also excluded.

Diagnostic Definitions

The reference diagnosis used in this study is the overall diagnosis provided by the pediatricians on the basis of clinical presentation, laboratory tests, chest X-ray, and the clinical course of the disease. An X-ray was performed only on subjects clinically suspected of pneumonia and, on other occasions, where there is clear need for it.

Therefore, not all our subjects underwent a chest X-ray.

Study Protocol

All children who satisfied the inclusion criteria were invited to participate in the study. Each child's history and clinical measurements were recorded as part of the hospital admission process. Diagnostic outcomes and all test results collected from the subjects in the course of normal diagnosis/management of the disease were made available to this study. Table 7 (Supplementary) lists some of the information recorded which was used for analysis in this paper.

TABLE 7

List of clinical parameters recorded at the time of admission

| History | Recorded details | Examination | Recorded details |
| --- | --- | --- | --- |
| Fever | Yes/No | Age | Months |
| Days with fever | Days | Weight | Kg |
| Cough | Yes/No | Height | m |
| Days with cough | Days | Breathing rate | Breaths/min |
| Runny nose | Yes/No | Heart rate | Beats/min |
| Days with runny nose | Days | Temperature | ° C. |
| Breathing difficulty | Yes/No | BMI | Number |
| Days with breathing difficulty | Days | Oxygen saturation | Percentage |
| | | Chest indrawing | Yes/No |

The test parameters included the existence of fever, cough, breathing difficulty, runny nose, and chest indrawing as a binary yes/no observation. It also included the following data as numbers: age, weight, height, breathing rate, temperature, BMI, oxygen saturation, and number of days suffering fever, cough, breathing difficulty, runny nose. Other diagnostic measures such as blood/sputum analysis and chest X-ray were performed only if the attending physician deemed it to be necessary.

Study Population

We recruited 222 children in total: 93 females, 129 males with a median age of 9 months and an inter-quartile range (IQR) of 4.25-20 months. Our population came from subjects admitted to the hospital ward. Our intention was to focus on the clinical parameters of interest in diagnosing pneumonia in resource poor regions. The dataset comprised 134 children with the complete list of parameters specified earlier. We excluded 88 patients from further consideration due to the absence of one or more of the required parameters. The distribution of the chosen 134 children closely represented the initial 222 children recruited, as shown in Table 8.

TABLE 8

Children representation between initial recruitment and actual number in study

| Category | Initial Recruitment (n = 222) | Model Building (n = 134) |
|---|---|---|
| Age | | |
| Median | 10 months | 11 months |
| IQR | 17 months | 21 months |
| Diagnosis Ratio | 2.47:1 | 2.62:1 |
| Pneumonia | 158 patients | 96 patients |
| Non-Pneumonia | 64 patients | 38 patients |
| Gender Ratio (M/F) | 1.39:1 | 1.27:1 |
| Male | 128 patients | 75 patients |
| Female | 92 patients | 59 patients |
| Age Group | | |
| <2 Months | 13 subjects | 0 subjects |
| 2-11 Months | 109 subjects | 71 subjects |
| 12-60 Months | 100 subjects | 63 subjects |

There were 71 and 63 children in the age groups 2-11 months and 12-60 months, respectively. Of the 134 children, 96 were diagnosed with pneumonia, whereas the remaining 38 were a mix of asthma, bronchitis, bronchiolitis, heart disease, malnutrition, wheezing, etc.

The non-pneumonia group served as the control set for this study.

Analysis of Data

Figure 13:
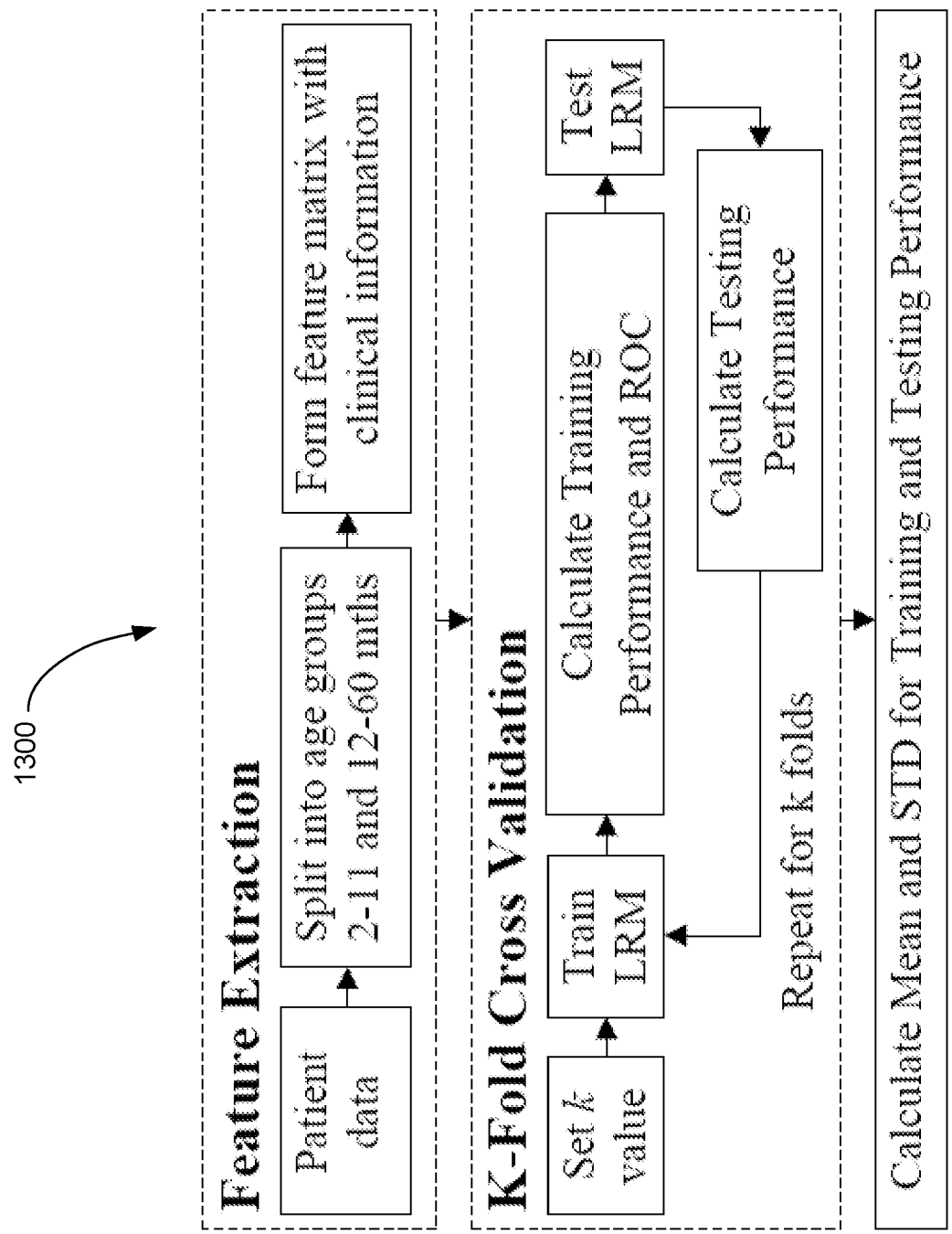
FIG. 13 is a flow diagram illustrating a method for training a diagnostic model for use in an embodiment of the present invention.

The flow diagram 1300 presented in FIG. 13 details the process used in analysing our data. The data set is split into two age groups, 2-11 months and 12-60 months.

Clinical features from each group are tabled into a feature matrix for processing.

Using a k-fold cross validation method, each age group was randomly split into k number of folds. An iterative process was then adopted in which one fold of data was retained as the testing set whilst the rest of the data was used for training a logistic regression model (LRM). A good general explanation of the logistic regression method used in medical applications can be found in a paper by K. L. Sainani[26].

The LRM outputs the probability of the existence of pneumonia based on the specified predictors, to which a cut-off threshold is applied to make the output a binary decision. This threshold was carefully selected following a receiver operating characteristic (ROC) analysis to separate the positive and negative pneumonia cases as cleanly as possible.

In the LRM design, we commenced by using one feature at a time and computing the performance of the resulting models. We then exhaustively searched all combinations of two features taken at a time. This process was continued until we reached all 17 features taken at a time. In each iteration, the trained models were evaluated according to their sensitivity ($S_n$), specificity ($S_p$), accuracy ($A_{cc}$), and the area under the curve (AUC). AUC was only available for the training data to set the diagnostics threshold.

Note that in each fold of the k-fold cross validation, the data set was divided into non-overlapping training and testing sets, and the performance was estimated separately for both the training and testing sets. Each iteration generated k number of ROC curves and k sets of training and testing performance measures. Each iteration also generated k number of trained LRM models. The trained LRM models were used to calculate the performance of the training set. The LRM models were then fixed, and used on the testing data set to compute the testing performance and validate the trained model. Each set of LRM models was considered final for its respective fold. Hence, for testing performance, no AUC data were available.

The best performing models were chosen based on the means and standard deviations (SD) of the training and testing performances. These numbers were calculated and are reported in the Results section. Similarly, the WHO criteria performance numbers were calculated for the testing sets and represented using their means and SDs. We then used the performance values to determine which parameters, in which combinations could provide the best diagnostic outcomes with the testing sets.

This process was iterated for each feature combination used. First we analyzed the LRM performance of using one, two, and three features at a time. Next, we exhaustively analyzed all possible feature combinations with up to 17 features being used at once. Table 9 shows the possible combinations for each number of features used in the creation of the LRM model.

TABLE 9

Total number of feature combinations possible out of 17 features available.

| No of Features | No of possible Combinations |
|---|---|
| 1 | 17 |
| 2 | 136 |
| 3 | 680 |
| 4 | 2,380 |
| 5 | 6,188 |
| 6 | 12,376 |
| 7 | 19,448 |
| 8 | 24,310 |
| 9 | 24,310 |
| 10 | 19,448 |
| 11 | 12,376 |
| 12 | 6,188 |
| 13 | 2,380 |
| 14 | 680 |
| 15 | 136 |
| 16 | 17 |
| 17 | 1 |
| Total | 131,071 |

Using one feature at a time gives 17 possible combinations, whereas using all 17 features at a time would have only one possible combination. The number of possible combinations rises significantly in between. For example, the use of 8 features at a time results in 24,310 combinations. In total, the number of models tested in this study is comprised of 131,071 combinations. Given the large number of models tested, the ROC curve analysis to find the best cut-off threshold for each model becomes very important. We selected the threshold targeting a $S_n \geq 90\%$ with $S_p$ as high as possible. This also had the benefit of lowering the false discovery rate (FDR). As we mentioned earlier, our aim is to improve the $S_p$ of the WHO procedure, while maintaining high $S_n$.

Results

In this section, we show the results of our analysis, starting from the cross-validation process and the WHO/IMCI procedure performance in our patient groups. We then describe the performance of our models and compare with the WHO outcomes in the 2-11 month age group, followed by the 12-60 month age group.

The Cross-Validation Technique

As detailed in Methods section, we use k-fold cross-validation to train and evaluate our classifier models. In this study we set k=8, resulting in 8-9 children in each fold. Higher k values, such as the more commonly used k=10, would result in 6-7 children in each fold. We deemed this number as insufficient and decided k=8 gives better balance for the testing data. Note that in each fold of the cross validation, training and testing sets are mutually exclusive, that is training and test testing sets do not overlap.

WHO/IMCI Performance

We applied the WHO criteria (see Table I) to data in each fold of the k-fold cross validation data set, and computed the mean and the standard deviation (SD) across all folds. Results are shown in Table 10.

TABLE 10

WHO criteria as applied to k-fold testing sets (Expressed in mean +/− standard deviation)

| Age Group | | Classification Performance (%) | | | | |
|---|---|---|---|---|---|---|
| | | $S_n$ | $S_p$ | $A_{cc}$ | PPV | NPV |
| 2-11 mth | Mean | 92.0 | 38.1 | 69.1 | 67.6 | 76.2 |
| | SD | 11.6 | 18.5 | 11.2 | 12.5 | 28.0 |

TABLE 10-continued

WHO criteria as applied to k-fold testing sets (Expressed in mean +/− standard deviation)

| Age Group | | Classification Performance (%) | | | | |
|---|---|---|---|---|---|---|
| | | $S_n$ | $S_p$ | $A_{cc}$ | PPV | NPV |
| 12-60 mth | Mean | 95.7 | 9.8 | 66.5 | 66.5 | 60.0 |
| | SD | 7.6 | 13.1 | 12.8 | 15.2 | 49.0 |

As expected, WHO criteria yielded high $S_n$ with relatively small SD across both age groups, but at a poor specificity $S_p$.

Our target is to maintain the high sensitivity of the WHO procedure while increasing the specificity. Next we describe the performance of the proposed method. As the analysis was done separately for each age group, we will begin by presenting the results for the 2-11 month age group.

Performance in the 2-11 Month Age Group

Figure 14A:
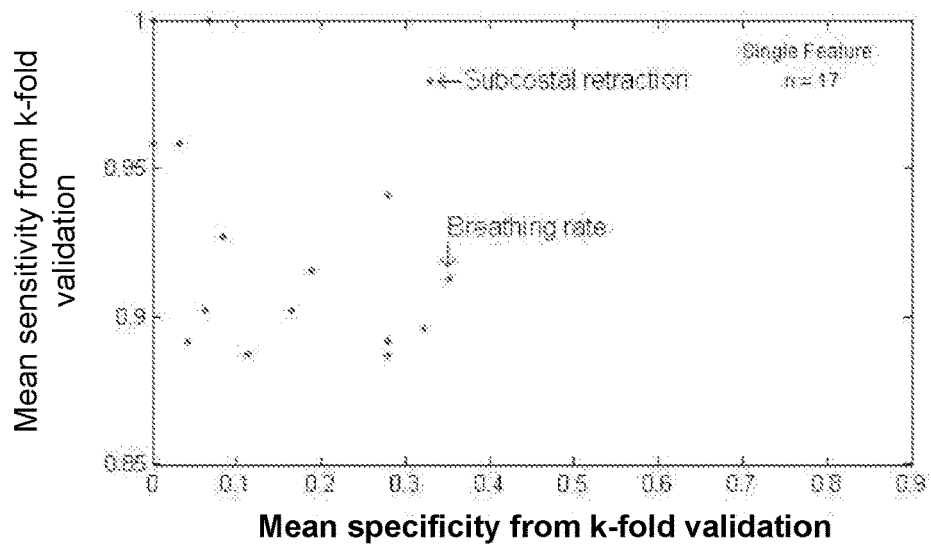
FIG. 14 comprises graphs representing mean Sn (sensitivity) and Sp (specificity) values from training models calculated from the age group 2-11 month. Frames from top to bottom are arranged by the number of features used to create the model: one (top), two (middle), and three features (bottom) taken at a time. n is the number of possible feature combinations using one, two, three features at a time. Significant improvements in specificity can be seen as more features were used.
Figure 14B:
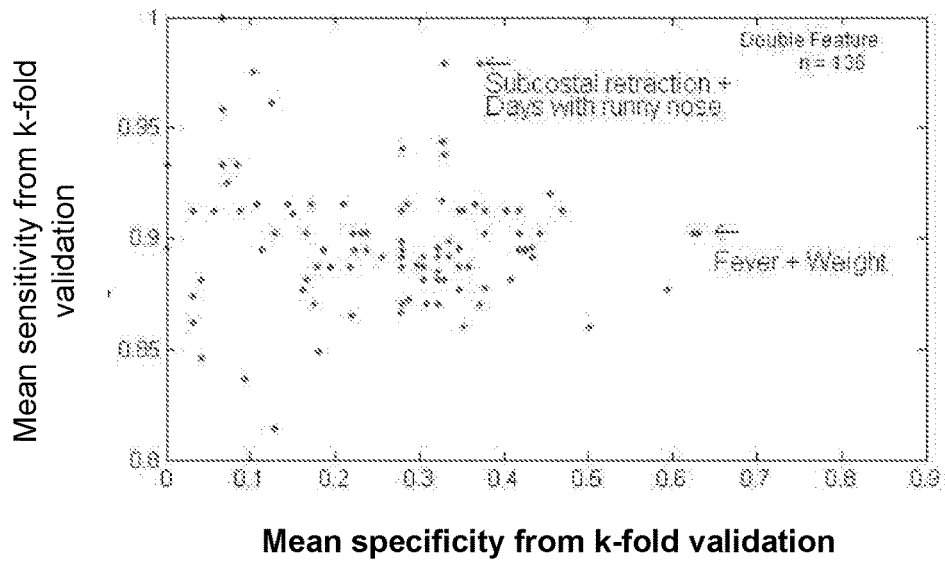
Figure 14C:
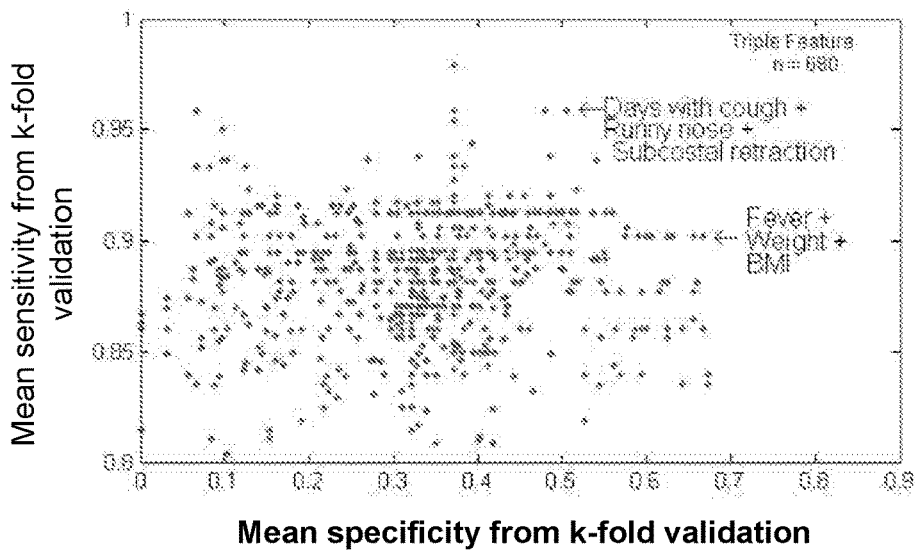

FIGS. 14A to 14C show mean $S_n$ and $S_p$ values for models using one, two, and three features at a time for the 2-11 month age group. Our feature set consisted of 17 observations/measurements as listed in Table 11. The number of total combinations of one-feature taken at a time is 17, leading to 17 LRM models with one feature as the input (FIG. 14A). Similarly, two features at a time and three features at a time give us 136 and 680 LRM models respectively (FIG. 14B and FIG. 14C bottom frames). Overall, significant benefits were found in combining features up to four at a time in one LRM.

Figure 15:
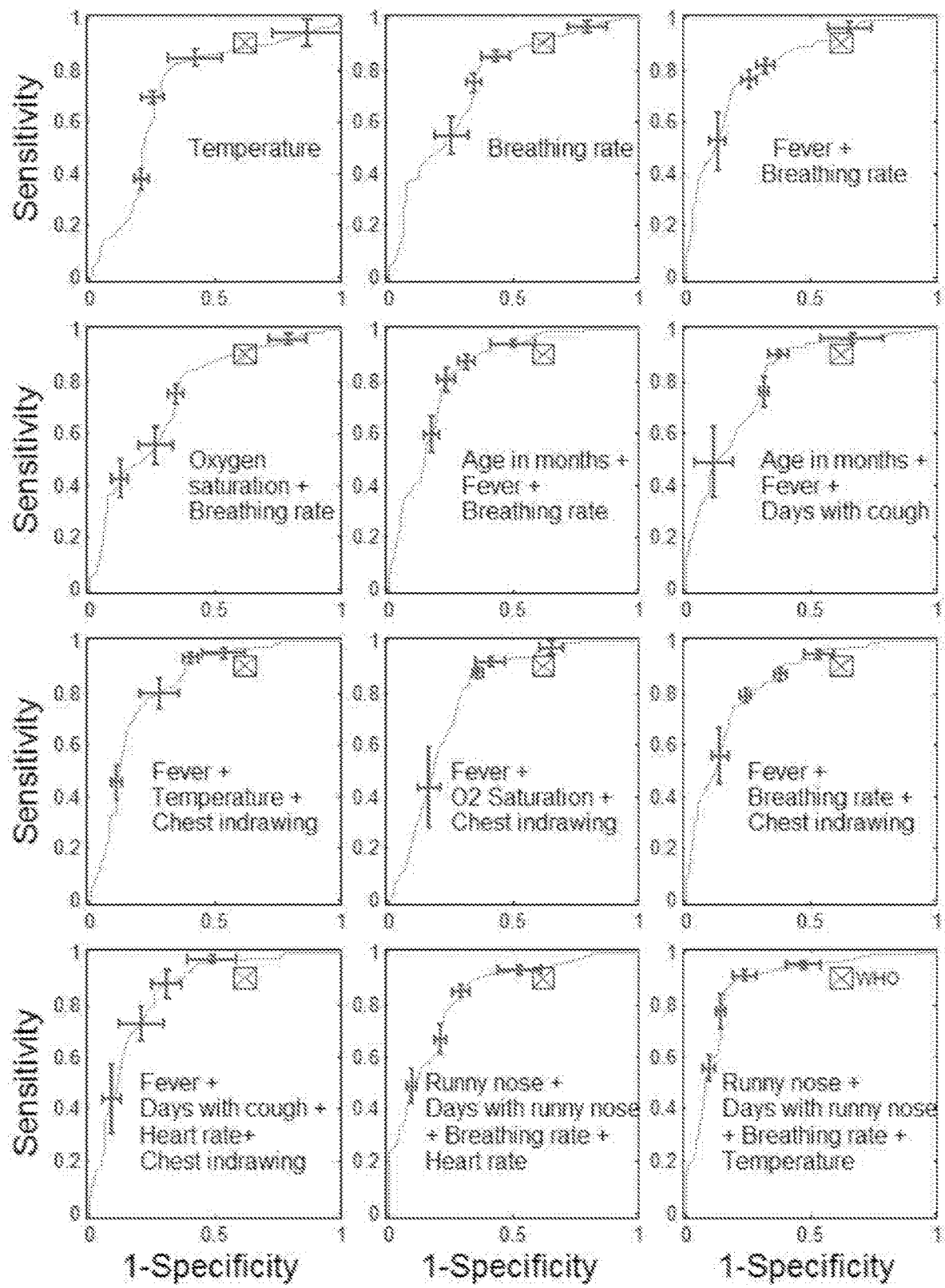
FIG. 15 comprises ROC curve analysis for the age group of 2-11 month. The solid line in each frame represents the mean ROC curve, formed over k-iterations. Crosses on each frame represent the SD of the Sn and 1-Sp at points shown. On each frame, the performance of WHO/IMCI procedure for resource-limited regions is graphically illustrated (see boxes). The center of the box indicates the mean performance, and the height and width of the box represent SD.

FIG. 15 shows the ROC curve analysis for 12 trained LRM models we selected for further consideration. Two models each are from single and double feature combinations, five from triple feature combinations, and three with four feature combinations. The solid line in each frame represents the mean ROC curve, formed over the k folds. Crosses on each frame represent the SD of the $S_n$ and $1-S_p$ at points shown. On each frame of FIG. 15, we also graphically illustrate (see boxes) the performance possible with the WHO/IMCI procedure for resource-limited regions. The centre of the box indicates the mean performance, and the height and width of the box represent SD. Table 11 shows the training and testing performance numbers for the 12 models.

TABLE 11

Performance comparison between various models for diagnosing pneumonia in children aged 2-11 months (AUC = Area Under Curve, CO = Cut-Off threshold).

| Features | | Training Performance (%) | | | | | Testing Performance (%) | | |
|---|---|---|---|---|---|---|---|---|---|
| | | $S_n$ | $S_p$ | $A_{cc}$ | AUC | CO | $S_n$ | $S_p$ | $A_{cc}$ |
| Temperature | Mean | 93.2 | 11.9 | 59.9 | 71.7 | 38.4 | 88.8 | 11.3 | 58.7 |
| | SD | 1.4 | 9.8 | 3.9 | 2.5 | 3.7 | 13 | 12.2 | 12.2 |
| Breathing rate (BR) | Mean | 93.5 | 35.4 | 69.8 | 74.9 | 35.6 | 91.3 | 35.2 | 65.7 |
| | SD | 1.5 | 12 | 4.3 | 2.2 | 2.5 | 13 | 29.8 | 17.1 |
| Chest indrawing | Mean | 97.6 | 34.4 | 71.8 | 66 | 67.9 | 97.9 | 32.9 | 71.6 |
| | SD | 1 | 3.4 | 1.6 | 1.8 | 1.8 | 5.9 | 23.7 | 10.7 |
| Fever + Breathing rate | Mean | 93.2 | 44.5 | 73.2 | 82.1 | 33.5 | 86 | 50.2 | 69.1 |
| | SD | 1.5 | 11.2 | 4.7 | 2.6 | 3.7 | 17.9 | 26.6 | 18.2 |
| Oxygen(O2) saturation + Breathing rate | Mean | 91.8 | 37.9 | 69.8 | 75.0 | 37.2 | 91.2 | 35.2 | 65.7 |
| | SD | 0.3 | 11.6 | 5.0 | 2.3 | 3.4 | 13.0 | 29.8 | 17.0 |
| Age (months) + Fever + Breathing rate | Mean | 91.8 | 63.7 | 80.3 | 83.3 | 39.9 | 86 | 66.7 | 76.6 |
| | SD | 0.3 | 7.9 | 3.4 | 2.4 | 5.1 | 17.9 | 22.5 | 16.8 |
| Age (months) + Fever + Days with cough | Mean | 91.8 | 63.7 | 80.3 | 81.2 | 41.3 | 83.5 | 67.3 | 76.1 |
| | SD | 0.3 | 4.5 | 2.4 | 1.9 | 10.6 | 14.5 | 23.9 | 18.5 |
| Fever + Temperature + Chest indrawing | Mean | 91.8 | 62.1 | 79.7 | 82.6 | 46 | 90.6 | 57.7 | 77.8 |
| | SD | 0.3 | 1.2 | 0.8 | 1.8 | 5.6 | 13.7 | 13 | 10.6 |
| Fever + O2 saturation + Chest indrawing | Mean | 92.8 | 64 | 81.1 | 77.9 | 44.1 | 88.1 | 61.9 | 77.6 |
| | SD | 1.5 | 3 | 1.6 | 1.9 | 8.7 | 13.6 | 8.7 | 10.9 |
| Fever + Breathing rate + | Mean | 91.8 | 59.2 | 78.5 | 83.6 | 41.4 | 86 | 56.3 | 73.6 |

TABLE 11-continued

Performance comparison between various models for diagnosing pneumonia in
children aged 2-11 months (AUC = Area Under Curve, CO = Cut-Off threshold).

| Features | | Training Performance (%) | | | | | Testing Performance (%) | | |
|---|---|---|---|---|---|---|---|---|---|
| | | $S_n$ | $S_p$ | $A_{cc}$ | AUC | CO | $S_n$ | $S_p$ | $A_{cc}$ |
| Chest indrawing | SD | 0.3 | 4.7 | 2.2 | 2.1 | 4.3 | 17.9 | 10.1 | 14.1 |
| Fever + Days with cough + | Mean | 92.2 | 65.9 | 81.5 | 84.7 | 59.6 | 86.0 | 63.5 | 76.3 |
| Heart rate + Chest indrawing | SD | 1.0 | 6.5 | 2.6 | 2.6 | 7.9 | 15.5 | 18.6 | 13.3 |
| Runny nose + Days with | Mean | 91.8 | 77.4 | 85.9 | 88.1 | 51.0 | 91.3 | 70.2 | 82.0 |
| runny nose + BR + Temp | SD | 0.3 | 6.1 | 2.5 | 2.1 | 6.1 | 13.0 | 22.8 | 9.3 |
| Runny nose + Days wish | Mean | 91.8 | 64.0 | 80.5 | 83.5 | 41.5 | 91.5 | 66.0 | 80.1 |
| runny nose + BR + Heart rate | SD | 0.3 | 4.6 | 2.0 | 2.2 | 2.6 | 9.2 | 26.3 | 12.1 |

When a single feature is used to create the LRM for the 2-11 month age group, the best features in terms of testing performance were breathing rate ($S_n$ of 91% and $S_p$ of 35%) and chest in-drawing ($S_n$ of 98% and $S_p$ of 33%). These numbers closely matched the performance of the WHO criteria, as it also relies on the same features for childhood pneumonia classification.

Individually, the breathing rate and temperature exhibit the highest AUC in the training performance. However, the temperature model shows high $S_n$ and lower $S_p$ compared to the WHO criteria, as opposed to breathing rate model which has comparable numbers. On the testing dataset, both models demonstrate high $S_n$ with little SD, but the SDs of the $S_p$ vary wildly, rendering both models unusable by themselves. This suggests that the WHO criteria are still more reliable when compared to single feature LRM models.

The use of two features at a time boosts the $S_p$ to 50% for certain feature combinations while maintaining $S_n$ around 90%. This is a significant improvement from the $S_p$ of the best single feature model. The best performers are models using breathing rate with oxygen saturation, and, breathing rate with fever. Both feature combinations exhibit high AUC (75-82%) in training.

We continued to add features further until the optimal LRM feature combinations were found. On the three simultaneous feature models, the overall testing performances are higher than the double feature ones. Mean $S_n$ levels remain largely the same around 90% and mean $S_p$ levels are on average 30% higher than the double feature models. The SD levels for $S_n$ is unchanged but for $S_p$ is 44% smaller. The best performing model for this category includes fever, oxygen saturation and chest in-drawing as parameters, achieving a $S_n$ value of 88.1±13.6% and an $S_p$ value of 61.9±8.7%. Compared to WHO/IMCI procedure ($S_n$ and $S_p$ of 92.0±11.6% and 38.1±18.5%, respectively), the mean $S_n$ is 4% lower while $S_p$ is 62% higher. The SDs are 17% larger for $S_n$ and 53% smaller for $S_p$ compared to WHO. Thus, the best triple feature model performs much better than WHO criteria in terms of $S_p$, with a small loss of $S_n$.

Further improvements in classification performance are found using four features at a time. The best performing model uses the existence of runny nose, number of days with runny nose, breathing rate and temperature (91.3±13.0% $S_n$ and 70.2±22.80% $S_p$). The mean $S_n$ is on a par with the WHO results, and the mean $S_p$ is 84% higher. The SD for both $S_n$ and $S_p$ are, however, slightly higher compared to WHO/IMCI procedure. The second best performing model uses runny nose, days with runny nose, breathing rate, and heart rate at $S_n$ of 91.5±9.2% and $S_p$ of 66.0±26.3%. The mean $S_n$ is also on a par with the WHO results while $S_p$ is 73% higher. For SDs, they are 20% smaller for $S_n$ and 42% larger for $S_p$ compared to WHO.

Performance in the 12-60 Month Age Group

Figure 16:
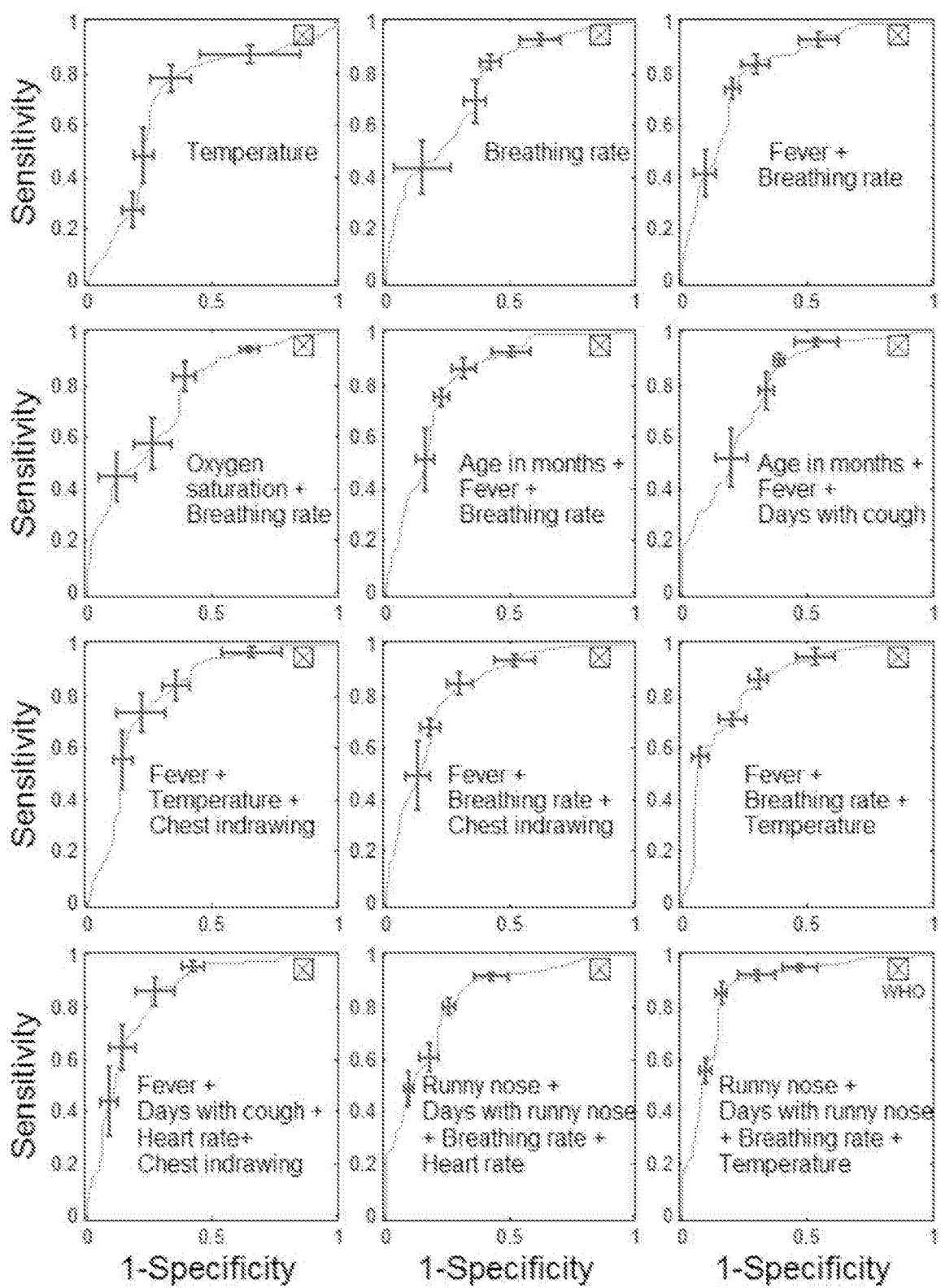
FIG. 16 comprises ROC curve analysis for the age group of 12-60 month. The solid line in each frame represents the mean ROC curve, formed over k-iterations. Crosses on each frame represent the SD of the Sn and 1-Sp at points shown. On each frame, the performance of WHO/IMCI procedure for resource-limited regions is graphically illustrated (see boxes). The center of the box indicates the mean performance, and the height and width of the box represent SD.

For the 12-60 month age group, the same process is repeated, starting with observation of the ROC curves from 12 trained LRM models chosen for comparison, as shown in FIG. 16, which is a ROC curve analysis for the age group of 12-60 month. The solid line in each frame represents the mean ROC curve, formed over k-iterations. Crosses on each frame represent the SD of the $S_n$ and $1-S_p$ at points shown. On each frame, the performance of WHO/IMCI procedure for resource-limited regions is graphically illustrated by the crossed boxes. The center of the box indicates the mean performance, and the height and width of the box represent SD.

TABLE 12

Performance comparison between trained models and WHO criteria for children
aged 12-60 months (AUC = Area Under Curve, CO = Cut-Off threshold).

| Features | | Training Performance (%) | | | | | Testing Performance (%) | | |
|---|---|---|---|---|---|---|---|---|---|
| | | $S_n$ | $S_p$ | $A_{cc}$ | AUC | CO | $S_n$ | $S_{pA}$ | $A_{cc}$ |
| Temperature | Mean | 93.0 | 10.7 | 64.4 | 70.4 | 46.6 | 88.0 | 19.2 | 61.6 |
| | SD | 1.6 | 13.6 | 3.9 | 2.6 | 3.2 | 14.0 | 35.0 | 35.0 |
| Breathing rate | Mean | 93.0 | 41.5 | 75.1 | 74.9 | 42.6 | 88.2 | 45.2 | 71.2 |
| (BR) | SD | 1.6 | 9.4 | 2.9 | 2.8 | 4.2 | 14.6 | 32.0 | 15.2 |
| Chest indrawing | Mean | 97.6 | 32.0 | 74.6 | 64.8 | 72.3 | 97.5 | 32.3 | 74.3 |
| | SD | 1.0 | 4.9 | 3.0 | 2.5 | 3.0 | 7.1 | 35.8 | 20.6 |
| Fever + | Mean | 92.0 | 49.6 | 77.3 | 82.0 | 41.4 | 88.3 | 44.2 | 67.9 |
| Breathing rate | SD | 1.1 | 10.5 | 3.1 | 2.4 | 5.9 | 15.2 | 47.7 | 21.1 |
| Oxygen(O2) saturation + | Mean | 91.6 | 47.0 | 76.0 | 79.3 | 46.5 | 88.2 | 57.7 | 72.2 |
| Breathing rate | SD | 0.4 | 6.5 | 3.2 | 2.7 | 6.5 | 14.6 | 31.3 | 17.5 |

TABLE 12-continued

Performance comparison between trained models and WHO criteria for children aged 12-60 months (AUC = Area Under Curve, CO = Cut-Off threshold).

| Features | | $S_n$ | $S_p$ | $A_{cc}$ | AUC | CO | $S_n$ | $S_{pA}$ | $A_{cc}$ |
|---|---|---|---|---|---|---|---|---|---|
| | | Training Performance (%) | | | | | Testing Performance (%) | | |
| Age (months) + Fever + | Mean | 91.6 | 58.4 | 80.0 | 81.5 | 46.9 | 88.3 | 70.6 | 75.9 |
| Breathing rate | SD | 0.4 | 10.3 | 3.6 | 2.5 | 7.2 | 15.2 | 33.5 | 14.9 |
| Age (months) + Fever + | Mean | 91.6 | 60.4 | 80.7 | 79.3 | 53.5 | 84.3 | 59.6 | 74.6 |
| Days with cough | SD | 0.4 | 4.3 | 2.0 | 2.2 | 9.4 | 21.2 | 37.6 | 13.4 |
| Fever + Temperature + | Mean | 92.0 | 57.7 | 80.0 | 80.6 | 51.8 | 92.1 | 51.3 | 79.2 |
| Chest indrawing | SD | 0.9 | 3.8 | 1.4 | 2.6 | 9.7 | 15.8 | 39.0 | 16.5 |
| Fever + Breathing rate + | Mean | 91.6 | 56.4 | 79.4 | 82.3 | 49.0 | 88.3 | 58.1 | 74.3 |
| Chest indrawing | SD | 0.4 | 9.6 | 3.3 | 2.4 | 9.1 | 15.2 | 39.2 | 17.0 |
| Fever + Breathing rate | Mean | 92.0 | 61.1 | 81.2 | 85.5 | 42.1 | 87.9 | 74.8 | 77.5 |
| Temperature | SD | 0.9 | 7.9 | 3.0 | 1.7 | 5.1 | 15.4 | 30.2 | 16.9 |
| Fever + Days with cough + | Mean | 91.6 | 68.3 | 83.4 | 82.7 | 62.1 | 94.0 | 74.0 | 84.4 |
| Heart rate + Chest indrawing | SD | 0.3 | 6.6 | 2.7 | 3.4 | 7.7 | 12.1 | 23.3 | 8.8 |
| Runny nose + Days with | Mean | 91.6 | 74.0 | 85.5 | 87.5 | 52.3 | 91.4 | 71.9 | 87.5 |
| runny nose + BR + Temp | SD | 0.3 | 4.9 | 1.7 | 2.8 | 9.8 | 12.1 | 36.4 | 9.2 |
| Runny nose + Days with | Mean | 91.6 | 61.8 | 81.2 | 84.0 | 47.6 | 85.9 | 59.4 | 74.6 |
| runny nose + BR + Heart rate | SD | 0.3 | 3.2 | 1.6 | 2.8 | 3.3 | 21.2 | 37.6 | 17.7 |

Figure 17:
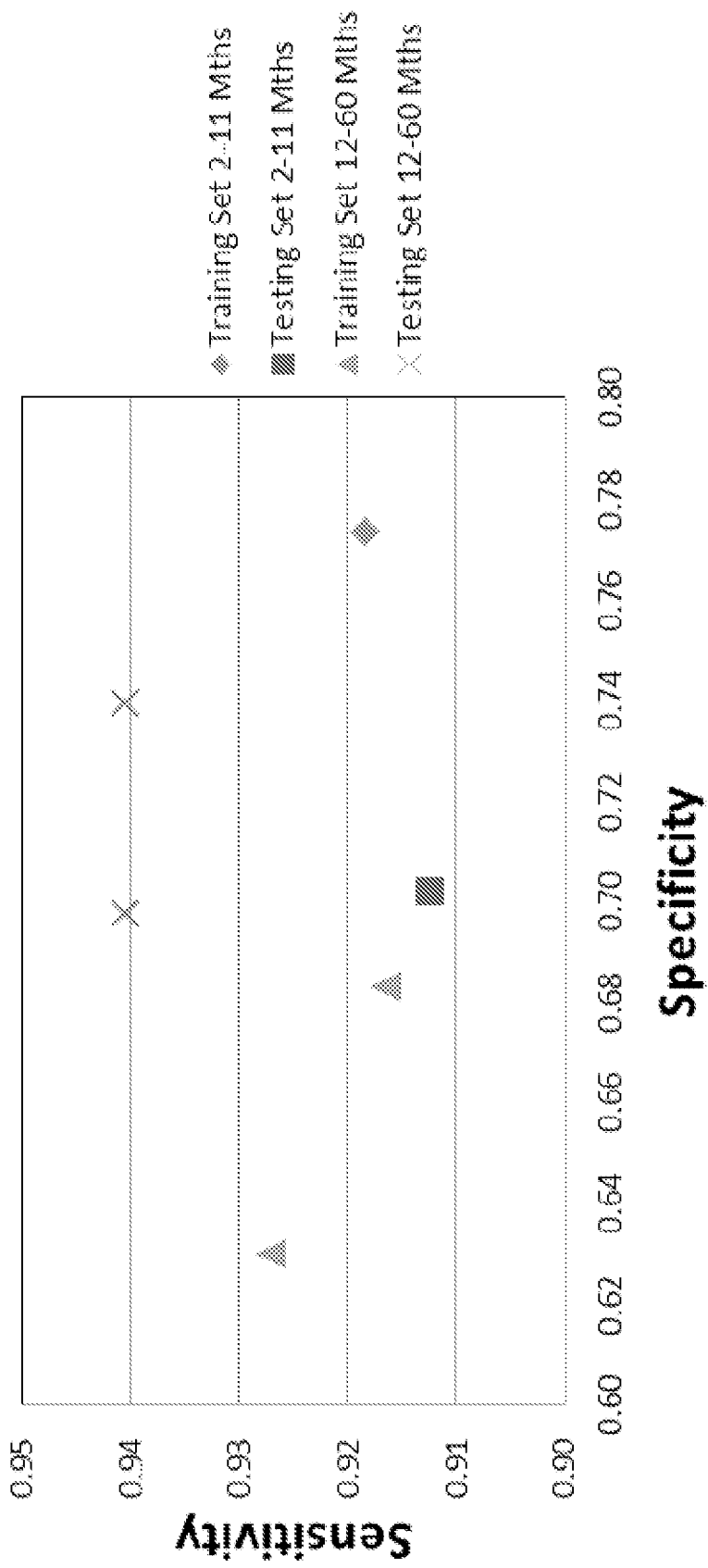
FIG. 17 is a graph showing the training and testing performance of the two best LRM models for 2-11 months and 12-60 months age group. The best LRM models for 2-11 months group were models using runny nose/days with runny nose/breathing rate/temperature and runny nose/days with runny nose/breathing rate/heart rate features. As for the 12-60 months group, the best models were based on fever/days with cough/heart rate/chest indrawing and runny nose/days with runny nose/breathing rate/temperature feature combinations.

The two best performing models for both age groups are compared in FIG. 17.

For the single feature category, breathing rate and chest in-drawing (individually) still exhibit the best performance in general. The WHO/IMCI procedure implementation for this age group demonstrates $S_n$ of 95.7±7.6% and $S_p$ of 9.8±13.1%. The best double feature LRM models in this age group also include breathing rate as a parameter. The best two models are breathing rate with fever and breathing rate with oxygen saturation.

For triple features, the best testing performance was observed when using fever, temperature, and chest in-drawing. This combination reached a $S_n$ of 92.1±15.8% and $S_p$ of 51.3±39.0% for testing performance. The mean $S_n$ is still comparable to the WHO criteria with 3% disparity, but the mean $S_p$ of the LRM model is 423% higher.

The SD of the $S_n$ is 107% larger compared to WHO, and for $S_p$ it is 197% greater. The best $S_p$ in this category is found in the combination of fever, breathing rate and temperature with $S_p$ of 74.8%±30.2%. This is a 663% increase of mean $S_p$ over WHO with 130% increase in SD. The mean $S_n$ value is also 8% lower compared to WHO results while SD remains 100% higher.

In models with four features, the best performing model uses the existence of fever, number of days with cough, heart rate, and existence of chest in-drawing ($S_n$ of 94.0±12.1% and $S_p$ of 74.0±23.3%). The mean $S_n$ is 2% lower than the WHO performance and the mean $S_p$ is 655% higher. The second best performing model utilizes runny nose, days with runny nose, breathing rate, and temperature with $S_n$ and $S_p$ of 91.4±12.1% and 71.9±36.4%, respectively.

Recurrent Features in Best Performing Models

Following the recurrent appearance of certain features amongst the best performing LRMs in all feature combinations, we decided to systematically explore these features in order to rank the most significant features out of the 17 considered.

We set a threshold $S_n$ of 90% and $S_p$ of 70% on the mean testing performance for all possible combinations, from using one feature at a time to 17 features, and found 20 models that meet the criteria (eight models from the 2-11 month age group and 12 from the 12-60 age month group, respectively). Table 13 shows the number of recurrence for each feature within the top 20 feature combinations.

TABLE 13

Number of feature occurrence in the models showing >90% Sn and >70% Sp.

| No | Feature Name | 2 to 11 mths | 60 mths |
|---|---|---|---|
| 1 | 'Ageinmonths' | 0 | 0 |
| 2 | 'Fever' | 0 | 4 |
| 3 | 'Dayswithfever' | 0 | 0 |
| 4 | 'Cough' | 0 | 1 |
| 5 | 'Dayswithcough' | 0 | 4 |
| 6 | 'Runnynose' | 8 | 8 |
| 7 | 'Dayswithrunnynose' | 8 | 8 |
| 8 | 'Breathingdifficulty' | 0 | 1 |
| 9 | 'Dayswithbreathingdifficulty' | 0 | 0 |
| 10 | 'Weight' | 0 | 0 |
| 11 | 'Height' | 0 | 0 |
| 12 | 'Breathingrate' | 8 | 8 |
| 13 | 'Heartrate' | 0 | 1 |
| 14 | 'Temperature' | 8 | 8 |
| 15 | 'BMI' | 4 | 5 |
| 16 | 'O2Saturation' | 4 | 4 |
| 17 | 'Chestdrawing' | 4 | 8 |

Several measurements such as the breathing rate and observations such as the existence of runny nose are dominantly present as recurrent features in good models.

Discussion

One particular aim of this study was to explore if common clinical observations and measurements could be utilized to diagnose pneumonia at specificities higher than possible with the WHO procedure, while maintaining the sensitivity of at least 90%. Our results have illustrated that this is indeed possible. Our best performing models demonstrated a sensitivity of 91% while achieving an $S_p$ in the range of 70-72% depending on the age of the subjects. These numbers represented 84-655% increase in $S_p$ compared to the WHO/IMCI procedure, which had $S_p$ ranging between 10-38%. Our results are based on k-fold cross validation, and the reported outcomes are thus not on the same data used to train a particular model.

The number of clinical observations and measurements needed to achieve a desired performance provides useful insight in designing clinical protocols targeting resource-poor areas. Results we obtained indicated that our single feature models perform similar to the WHO/IMCI procedure. Addition of second, third and fourth features significantly improve $S_p$ while $S_n$ continues to hold above 90%. Beyond four features, the calculation complexity rises without any performance gain.

One important contribution of this paper is the identification of most important clinical features and measurements that may substantially increase the accuracy of diagnosing pneumonia in resource-poor regions. We surveyed our exhaustive model database for the repeated appearance of features in models satisfying $S_n>90\%$ and $S_p>70\%$.

The breathing rate appeared as a feature in 16 models across both age groups. Oxygen saturation and chest in drawing too were important parameters appearing respectively in 8 and 12 models out of a total of 20. The significance of these measurements are well known among the medical and research communities. Our work uncovered two parameters of potential significance; "the existence of runny nose" and the "number of days with runny nose" both of which appeared in 16 out of 20 models, just like the breathing rate. The "existence of fever" also presented as a frequent parameter (4 out of 20 models) for the age group 12-60 months.

Breathing rate is the main measurement used in the WHO/IMCI procedure to diagnose pneumonia. While it appears an easy parameter to measure, it has been found difficult to achieve in resource-poor regions. Therefore, a major fraction of the global pneumonia diagnosis resources are allotted to improving technologies and protocols to measure the breathing rate[nn]. Without a reliable breathing rate measurement, the WHO/IMCI methods cannot be used in the field.

Our results suggest that while breathing rate is an important parameter, it is not essential to diagnose pneumonia. For instance, our model using the four features age, existence of fever, existence of cough and days of cough was capable of $S_n=83.5\pm14.5\%$ and $S_p=67.3\pm23.9\%$ respectively, for the 2-11 month age group. In the other age group, this model exhibited $S_n$ and $S_p$ of $91.7\pm17.8\%$ and $51.0\pm34.6\%$, respectively. Among two-feature models, the combination using fever and days with cough resulted in $S_n$ and $S_p$ of $90.2\pm14.0\%$ and $44.3\pm25.9\%$, respectively, for the 2-11 month age group. For the older age group, the model performed with $S_n=85.5\pm15.2\%$ and $S_p=41.9\pm47.7\%$. These results corroborate our previous observation that breathing rate may not add additional value when mathematical features derived from cough sounds are available for diagnosing pneumonia[31].

Recently there has been a renewed interest in the use of pulse oximetry in reducing childhood pneumonia mortality in resource-poor settings[27-29]. Hypoxemia is a diagnostic indicator for severe pneumonia and swift access to oxygen treatment could improve the prognosis, when available. In our exhaustive model building process, we found 8 of the 20 best models included oximetry as a feature. Oximetry can be a highly useful feature. However, our results suggest that we can substitute, in its place, simpler feature combinations when a pulse oximeter is not available in the field. Examples features are the existence of runny nose and the days of runny nose.

The WHO/IMCI criteria for resource-poor regions have been designed to be highly sensitive to detect pneumonia (94% for those aged <24 months, 62% for ≥24 months)[17]. A high number of false positive results also occur, reducing the specificity of the method (16-20%)[17]. In two of our previous works on children, we have seen WHO/IMCI performing at a sensitivity of 83% and a specificity of 47% (n=91)[25,31]. The WHO/IMCI criteria works well when applied by doctors in conjunction with clinical and radiological analysis, giving performances of 77-81% sensitivity and 77-80% specificity[32]. These numbers are comparable with what we obtained in this paper, though our method did not use laboratory or radiological measurements.

Low specificity of the WHO criteria can lead to rising antimicrobial resistance in communities and render antibiotics ineffective. It also wastes rare drug stocks and delays early treatment opportunities for diseases with symptom overlap (e.g. malaria)[10,33]. In low resource settings where only WHO/IMCI criteria are available, as many as 30% of cases had symptoms compatible with both malaria and pneumonia, necessitating dual treatment[34]. One of these treatments could be redundant. The method presented in this paper could potentially help with these issues by producing more accurate results, even in the absence of key parameters such as breathing rate.

The approach we took in this paper is unique. We systematically exhausted all possible feature combinations in our set of 17 features. Altogether we built and tested 131,071 models, each using different feature combinations. In the literature there are instances where WHO/IMCI procedure was augmented with one or two other handpicked clinical features (e.g. fever, oximetry) targeting manual interpretation. For instance, Cardoso et al in their 2010 study[17] added fever to WHO/IMCI procedure and illustrated the specificity increased up to 44% (age group <24 month) and 50% (age group 24-60 months). However, the sensitivity was reduced below that of WHO/IMCI. In particular, in the age group 24-60 months, neither the original WHO/IMCI nor the modified method could achieve sensitivity above 62%. The method we proposed can achieve a sensitivity above 90% while maintaining the specificity at the range 70-72%. No manual interpretation of features is necessary, and our method can provide a decision device.

In an independent development, Naydenova et al. published results on a method of combining several features using a machine learning approach[30]. They reported oxygen saturation, temperature, breathing rate and heart rate as leading to the best performance in their model (sensitivity 96.6%, specificity 96.4%). In our work, the same feature combination resulted in a much inferior performance (sensitivity 88.8%, specificity 40% in the age group 2-11 months; sensitivity 82.7% and specificity 35.4% in the age group 12-60 months).

One critical difference between our method and the one by Naydenova[30] is that they used healthy people as Control Subjects while we used children with respiratory symptoms satisfying inclusion criteria as our Control Subjects. Our Control Subjects were children who visited the hospital seeking treatment for illnesses with symptoms shared with pneumonia, but the medical diagnosis was they had different diseases. The research problem we explored was completely different from the one examined by Naydenova[30] and the results are thus not comparable. Separating normal children from pneumonia subjects is a much simpler problem compared to identifying pneumonia subjects from a group of children with a range of respiratory illnesses.

CONCLUSION

We have developed a method using logistic regression modelling to diagnose pneumonia based on various clinical features commonly recorded from patients. The LRM models we developed retain the high sensitivity of the WHO/IMCI procedure while increasing its mean specificity by 84% for the 2-11 month age group and 655% for the 12-60 month age group.

This study is currently limited by the number of subjects (n=134) involved in the study as well as the way pneumonia was diagnosed. The reference standard used in this study is the overall clinical diagnosis aided by auscultation, laboratory analysis and radiography (when deemed clinically necessary by the attending physician) and the clinical course of the subject's response to treatment. Due to the need limit radiation exposure to children, x-ray imaging was not performed on all subjects in the study.

REFERENCES

The disclosure of each of the following documents is hereby incorporated in its entirety by reference.

[1] Fullman N, Lim S, Dieleman J, Greenslade L, Graves C, Huynh C, et al. Pushing the Pace: Progress and Challenges in Fighting Childhood Pneumonia. (IHME) IfH-MaE, editor. Seattle, Wash.: IHME; 2014.

[2] Liu L, Oza S, Hogan D, Perin J, Rudan I, Lawn J E, et al. Global, regional, and national causes of child mortality in 2000-13, with projections to inform post-2015 priorities: an updated systematic analysis. The Lancet. 2015; 385(9966):430-40.

[3] UN. We Can End Poverty: Millenium Development Goals and Beyond 2105. 2015; Available from: http://www.un.org/millenniumgoals/childhealth.shml.

[4] Bryce J, Black R, Victora C. Millennium Development Goals 4 and 5: progress and challenges. BMC Medicine. 2013; 11(1):225.

[5] UN. The Millenium Development Goals Report 2014. New York: UN; 2014.

[6] Walker C L, Rudan I, Liu L, Nair H, Theodoratou E, Bhutta Z A, et al. Global burden of childhood pneumonia and diarrhoea. Lancet. 2013; 381(9875):1405-16.

[7] Madhi S A, Wals P D, Grijalva C G, Grimwood K, Grossman R, Ishiwada N, et al. The Burden of Childhood Pneumonia in the Developed World: A Review of the Literature. The Pediatric Infectious Disease Journal. 2013; 32(3):e119-e27.

[8] Rambaud-Althaus C, Althaus F, Genton B, D'Acremont V. Clinical features for diagnosis of pneumonia in children younger than 5 years: a systematic review and meta-analysis. The Lancet Infectious Diseases. 2015; 15(4):439-50.

[9] Qazi S, Were W. Improving diagnosis of childhood pneumonia. The Lancet Infectious Diseases. 2015; 15(4): 372-3.

[10] WHO. Antimicrobial resistance: global report on surveillance 2014. Geneva: World Health Organization; 2014.

[11] Lynch T, Bialy L, Kellner J D, Osmond M H, Klassen T P, Durec T, et al. A Systematic Review on the Diagnosis of Pediatric Bacterial Pneumonia: When Gold Is Bronze. PloS one. 2010; 5(8):e11989.

[12] Chang A B, Ooi M H, Perera D, Grimwood K. Improving the Diagnosis, Management, and Outcomes of Children with Pneumonia: Where are the Gaps? Frontiers in Pediatrics. 2013; 1:29.

[13] Esposito S, Principi N. Unsolved problems in the approach to pediatric community-acquired pneumonia. Curr Opin Infect Dis. 2012; 25(3):286-91.

[14] Rudan I, El Arifeen S, Bhutta Z A, Black R E, Brooks A, Chan K Y, et al. Setting Research Priorities to Reduce Global Mortality from Childhood Pneumonia by 2015. PLoS Med. 2011; 8(9):e1001099.

[15] WHO. Consultative meeting to review evidence and research priorities in the management of ARI. Geneva: World Health Organization; 2004.

[16] Scott J A G, Wonodi C, Moïsi J C, Deloria-Knoll M, DeLuca A N, Karron R A, et al. The Definition of Pneumonia, the Assessment of Severity, and Clinical Standardization in the Pneumonia Etiology Research for Child Health Study. Clinical Infectious Diseases: An Official Publication of the Infectious Diseases Society of America. 2012; 54(Suppl 2):S109-S16.

[17] Cardoso M-RA, Nascimento-Carvalho C M, Ferrero F, Alves FtM, Cousens S N. Adding fever to WHO criteria for diagnosing pneumonia enhances the ability to identify pneumonia cases among wheezing children. Arch Dis Child. 2011; 96(1):58-61.

[18] Wingerter S L, Bachur R G, Monuteaux M C, Neuman M I. Application of the World Health Organization Criteria to Predict Radiographic Pneumonia in a US-based Pediatric Emergency Department. The Pediatric Infectious Disease Journal. 2012; 31(6):561-4.

[19] Dreiseitl S, Ohno-Machado L. Logistic regression and artificial neural network classification models: a methodology review. Journal of Biomedical Informatics. 2002; 35(5-6):352-9.

[20] Stoltzfus J C. Logistic Regression: A Brief Primer. Academic Emergency Medicine. 2011; 18(10):1099-104.

[21] Shorr A F, Zilberberg M D, Reichley R, Kan J, Hoban A, Hoffman J, et al. Readmission Following Hospitalization for Pneumonia: The Impact of Pneumonia Type and Its Implication for Hospitals. Clinical Infectious Diseases. 2013.

[22] Aliberti S, Di Pasquale M, Zanaboni A M, Cosentini R, Brambilla A M, Seghezzi S, et al. Stratifying Risk Factors for Multidrug-Resistant Pathogens in Hospitalized Patients Coming From the Community With Pneumonia. Clinical Infectious Diseases. 2012; 54(4):470-8.

[23] Teka Z, Taye A, Gizaw Z. Analysis of risk factors for mortality of in-hospital pneumonia patients in Bushulo Major Health Center, Hawassa, Southern Ethiopia. Science. 2014; 2(5):373-7.

[24] Swarnkar V, Abeyratne U, Chang A, Amrulloh Y, Setyati A, Triasih R. Automatic Identification of Wet and Dry Cough in Pediatric Patients with Respiratory Diseases. Ann Biomed Eng. 2013; 41(5):1016-28.

[25] Kosasih K, Abeyratne U R, Swarnkar V, Triasih R. Wavelet Augmented Cough Analysis for Rapid Childhood Pneumonia Diagnosis. Biomedical Engineering, IEEE Transactions on. 2015; 62(4):1185-94.

[26] Sainani K L. Logistic Regression. PM&R. 2014; 6(12): 1157-62.

[27] Floyd J, Wu L, Hay Burgess D, Izadnegandar R, Mukanga D, Ghani A C. Evaluating the impact of pulse oximetry on childhood pneumonia mortality in resource-poor settings. Nature. 2015; 528(7580):553-59.

[28] Ginsburg A S, Delarosa J, Brunette W, Levari S, Sundt M, Larson C, et al. mPneumonia: Development of an Innovative mHealth Application for Diagnosing and Treating Childhood Pneumonia and Other Childhood Illnesses in Low-Resource Settings. PloS one. 2015; 10(10):e0139625.

[29] Emdin C A, Mir F, Sultana S, Kazi A, Zaidi A M K, Dimitris M C, et al. Utility and feasibility of integrating pulse oximetry into the routine assessment of young infants at primary care clinics in Karachi, Pakistan: a cross-sectional study. BMC Pediatrics. 2015; 15(1):1-11.

[30]. Naydenova E, Tsanas A, Casals-Pascual C, Vos M D, editors. Smart diagnostic algorithms for automated detection of childhood pneumonia in resource-constrained settings. Global Humanitarian Technology Conference (GHTC), 2015 IEEE; 2015 8-11 Oct. 2015.

Abeyratne U R, Swarnkar V, Setyati A, Triasih R. Cough Sound Analysis Can Rapidly Diagnose Childhood Pneumonia. Ann Biomed Eng. 2013; 41(11):2448-62.

Mulholland E K, Simoes E A, Costales M O, McGrath E J, Manalac E M, Gove S. Standardized diagnosis of pneumonia in developing countries. Pediatr Infect Dis J. 1992; 11(2):77-81. Epub 1992 Feb. 1.

Thaver D, Ali S A, Zaidi A K. Antimicrobial resistance among neonatal pathogens in developing countries. Pediatr Infect Dis J. 2009; 28(1 Suppl).

Källander K, Nsungwa-Sabiiti J, Peterson S. Symptom overlap for malaria and pneumonia—policy implications for home management strategies. Acta Tropica. 2004; 90(2):211-4.

WHO. Acute respiratory infections in children: Case management in small hospitals in developing countries: A manual for doctors and other senior health workers. Geneva: World Health Organization; 1990.

Puumalainen T, Quiambao B, Abucejo-Ladesma E, Lupisan S, Heiskanen-Kosma T, Ruutu P, et al. Clinical case review: A method to improve identification of true clinical and radiographic pneumonia in children meeting the World Health Organization definition for pneumonia. BMC Infect Dis. 2008; 8(1):95.

{nn} group:

nn1. The Acute Respiratory Infection Diagnostic Aid (ARIDA) Project, Unicef. http://www.unicef.org/innovation/innovation_81722.html (accessed on Aug. 3, 2016).

nn2. World's first pneumonia innovations summit unveils next generation prevention, diagnostic and treatment innovations, World Pneumonia Day-2015, http://www.malariaconsortium.org/news-centre/worlds-first-plieumenia-innovations-summit-unveils-next-generation-prevention-diagnostic-and-treatment-innovations.htm (accessed on Aug. 3, 2016).

nn3. Pneumonia Diagnostics Project, Malaria Consortium, http://www.malariaconsortium.org/projects/pneumonia-diagnostics (accessed on Aug. 3, 2016).

End of Appendix B

In compliance with the statute, the invention has been described in language more or less specific to structural or methodical features. The term "comprises" and its variations, such as "comprising" and "comprised of" is used throughout in an inclusive sense and not to the exclusion of any additional features. It is to be understood that the invention is not limited to specific features shown or described since the means herein described herein comprises preferred forms of putting the invention into effect. The invention is, therefore, claimed in any of its forms or modifications within the proper scope of the appended claims appropriately interpreted by those skilled in the art.

Throughout the specification and claims (if present), unless the context requires otherwise, the term "substantially" or "about" will be understood to not be limited to the value for the range qualified by the terms.

Any embodiment of the invention is meant to be illustrative only and is not meant to be limiting to the invention. Therefore, it should be appreciated that various other changes and modifications can be made to any embodiment described without departing from the spirit and scope of the invention.

The invention claimed is:

1. A method for automatically providing a caregiver of a patient with a disease state diagnosis of the patient, the method comprising:
    providing a diagnostic application software product including a multiplicity of diagnostic models derived from investigation of a population containing disease state positive and non-disease state subjects, wherein the diagnostic application software product when executed performs operations comprising:
        responsive to a first predefined set of general danger signs not being positive and a second predefined set of screening criteria being positive:
            prompting the caregiver, via an input/output interface of an electronic device including a memory storing the software product, for further patient data for the patient including prompting the caregiver to identify a plurality of diagnostic parameters;
            automatically selecting an optimal diagnostic model from the diagnostic models from the memory, based at least in part on the further patient data;
            applying at least the further patient data to the automatically selected optimal diagnostic model; and
            presenting a diagnosis to the caregiver on the input/output interface based at least in part on results of the application of at least the further patient data to the automatically selected optimal diagnostic model for the caregiver to use in providing therapy to the patient.

2. A method according to claim 1, wherein said diagnostic parameters comprise one or more of: breathing rate, existence of fever, existence of runny nose, number of days with runny nose, number of days with cough, existence of chest indrawing, temperature, BMI (body mass index), and oxygen saturation level.

3. A method according to claim 1, further comprising operating the electronic device to select one of the diagnostic models with reference to one or more look up tables correlating diagnostic performance of models against available diagnostic parameters.

4. A method according to claim 1, further comprising:
    prompting for user choice of a diagnostic model optimized for "sensitivity", "specificity" or "accuracy"; and
    operating the electronic device to select one of the diagnostic models taking into account the user choice.

5. A method according to claim 1, further comprising determining whether the values of diagnostic parameters indicate patient danger signs.

6. A method according to claim 5, wherein the first predefined set of general danger signs are general danger signs according to World Health Guidelines, and further comprising checking whether diagnostic values for the patient indicate that the patient is presenting general danger signs according to the World Health Guidelines.

7. A method according to claim 1, further comprising saving diagnostic results to a remote server so that diagnostic results are savable and comparable from a plurality of diagnostic devices.

8. A method according to claim 1, further comprising prompting for recording of at least one patient cough sound.

9. A method according to claim 8, further comprising prompting for no more than two patient cough sounds.

10. A method according to claim 8, further comprising applying the at least one patient cough sound to a cough feature extraction engine to generate patient cough features.

11. A method according to claim 10, wherein the patient cough features are applied to the diagnostic model to assist the diagnosis.

12. A method according to claim 1, wherein the diagnostic parameters comprise breathing rate, temperature, heart rate and cough sound analysis.

13. A diagnostic device arranged to prompt a clinician to input diagnostic information for a patient and further arranged to automatically present a diagnosis to the clinician, the diagnostic device including:
an electronic memory storing instructions comprising a diagnostic application software product and a plurality of diagnostic models derived from investigation of pneumonia-positive and non-pneumonia subjects;
an electronic processor in communication with the electronic memory, the electronic processor being configured to execute the instructions; and
a user interface responsive to the electronic processor;
wherein the instructions, when executed, perform operations comprising:
responsive to a first predefined set of general danger signs not being positive and a second predefined set of screening criteria being positive:
prompting the clinician, via the user interface, for further patient data for the patient including prompting the caregiver to identify a plurality of diagnostic parameters;
automatically selecting an optimal diagnostic model from the diagnostic models from the memory, based at least in part on the further patient data;
automatically applying at least the further patient data to the automatically selected optimal diagnostic model; and
presenting a diagnosis of the patient via the user interface to the clinician based at least in part on results of the application of at least the further patient data to the automatically selected optimal diagnostic model for the caregiver to use in providing therapy to the patient.

14. A diagnostic device according to claim 13, wherein the diagnostic device includes a microphone and audio interface coupling the microphone to the electronic processor for receiving a cough sound of the patient.

15. A diagnostic device according to claim 14, further comprising a cough feature extraction engine as part of the diagnostic application software product, wherein in use the processor is configured to apply the cough sound to the cough feature extraction engine to produce cough features thereof.

16. A diagnostic device according to claim 15, wherein the diagnostic device is controllable in use to apply the cough features to at least one of said diagnostic models.

17. A method of automatically diagnosing pneumonia in a patient, the method comprising:
responsive to a first predefined set of general danger signs not being positive and a second predefined set of screening criteria being positive:
prompting the caregiver, via an input/output interface coupled to an electronic device, to provide further patient data for the patient including prompting the caregiver to identify diagnostic parameters including two or more of breathing rate, existence of fever, existence of runny nose, number of days with runny nose, number of days with cough, existence of chest indrawing, temperature, Body Mass Index (BMI), and oxygen saturation level;
applying at least the further patient data to a plurality of precompiled pneumonia diagnostic models stored in an electronic memory to identify an optimal diagnostic model from the plurality precompiled pneumonia diagnostic models;
automatically applying at least the further patient data to the identified optimal diagnostic model to generate a diagnosis output; and
operating the input/output interface device in accordance with the diagnosis output to indicate presence or absence of pneumonia in the patient to the caregiver, for use by the caregiver in providing care to the patient;
wherein the pneumonia diagnostic models are derived from investigation of a population of pneumonia positive patients and non-pneumonia positive subjects.

18. A method according to claim 1, wherein the screening criteria comprise breathing difficulty, breathing rate, and/or one or more symptoms of cough.

19. A diagnostic device according to claim 13, wherein the screening criteria comprise breathing difficulty, breathing rate, and/or one or more symptoms of cough.

20. A method according to claim 17, wherein the screening criteria comprise breathing difficulty, breathing rate, and/or one or more symptoms of cough.

21. A diagnostic device according to claim 13, wherein a first determination that the first predefined set of general danger signs are not positive is made prior to a second determination that the second predefined set of screening criteria is positive, and
wherein the second determination is performed conditioned on the first determination indicating a lack of patient danger signs for the patient.

* * * * *